United States Patent [19]

Grauert et al.

[11] Patent Number: 5,053,430

[45] Date of Patent: Oct. 1, 1991

[54] USE OF 2,7-DIAMINO-1,2,3,4-TETRAHYDRONAPHTHALENES AS MEDICAMENTS, NEW 2,7-DIAMINO-1,2,3,4-TETRAHYDRONAPHTHALENES AND PROCESSES FOR THEIR PREPARATION

[75] Inventors: Matthias Grauert; Herbert Merz, both of Ingelheim am Rhein; Joachim Mierau, Mainz; Gunter Schingnitz, Bad Kreuznach; Claus Schneider, Eppelheim, all of Fed. Rep. of Germany

[73] Assignee: Boehringer Ingelheim KG, Ingelheim am Rhein, Fed. Rep. of Germany

[21] Appl. No.: 411,146

[22] Filed: Sep. 22, 1989

[30] Foreign Application Priority Data

Sep. 24, 1988 [DE] Fed. Rep. of Germany ....... 3832571

[51] Int. Cl.[5] ................. A61K 31/165; C07C 233/43; C07C 233/44
[52] U.S. Cl. ................. 514/630; 514/235.5; 514/236.8; 514/237.5; 514/253; 514/255; 514/317; 514/318; 514/319; 514/333; 514/354; 514/357; 514/369; 514/370; 514/444; 514/445; 514/447; 514/471; 514/472; 514/473; 514/533; 514/534; 514/538; 514/539; 514/542; 514/597; 514/602; 514/604; 514/629; 544/111; 544/124; 544/133; 544/146; 544/152; 544/159; 544/165; 544/358; 544/360; 544/369; 544/374; 544/379; 544/390; 546/187; 546/189; 546/205; 546/268; 546/284; 546/290; 546/293; 546/296; 546/297; 546/300; 548/182; 548/186; 548/187; 548/202; 548/204; 548/205; 549/62; 549/65; 549/66; 549/68; 549/74; 549/76; 549/475; 549/476; 549/478; 549/479; 549/480; 549/481; 549/482; 549/492; 549/494; 549/496; 560/13; 560/19; 560/28; 564/50; 564/90; 564/92; 564/99; 564/222; 564/428
[58] Field of Search ................. 564/222; 514/629, 630

[56] References Cited

U.S. PATENT DOCUMENTS

| 4,320,148 | 3/1982 | DeMarinis | 564/222 |
| 4,442,126 | 4/1984 | Beeley et al. | 514/629 |
| 4,520,030 | 5/1985 | Cavero et al. | 514/629 |

FOREIGN PATENT DOCUMENTS

| 0041488 | 12/1981 | European Pat. Off. |
| 0055043 | 6/1982 | European Pat. Off. |
| 0074903 | 3/1983 | European Pat. Off. |
| 0270947 | 6/1988 | European Pat. Off. |

OTHER PUBLICATIONS

Asselin et al., Drug Design via Pharmacophore Identification. Dopaminergic Activity of 3H-Benz[e]Indol-8-Amines and their Mode of Interaction with the Dopamine Receptor, J. Med. Chem. 29; 648–654 (1986).

A. Windaus, Uber Einige Derivate Des Ac.-Tetrahydro-$\beta$-Naphthylamins; Berichte Der Deutschen Chemischen Gesellschaft, 57; Jahrgang; 1924, Band II, pp. 1731–1739 (Verlag Chemie; GmbH. Leipzig and Berlin).

Beilsteins Handbuch Der Organischen Chemie, 4; Erganzungswerk, 13; Band, 1950–1959; 4, Auflage, p. 328 (Springer-Verlag Berlin, Heidelberg, New York; Tokyo 1985).

Primary Examiner—Glennon H. Hollrah
Assistant Examiner—Susan P. Treanor
Attorney, Agent, or Firm—D. E. Frankhouser; D. Reitenbach; M-E. M. Timbers

[57] ABSTRACT

Novel compounds having the general formula

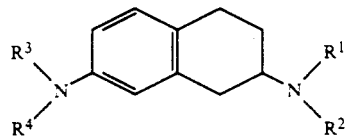

wherein $R^1$, $R^2$, $R^3$ and $R^4$ are as defined herein. These compounds are useful in the treatment of schizophrenia.

6 Claims, No Drawings

USE OF 2,7-DIAMINO-1,2,3,4-TETRAHYDRONAPHTHALENES AS MEDICAMENTS, NEW 2,7-DIAMINO-1,2,3,4-TETRAHYDRONAPHTHALENES AND PROCESSES FOR THEIR PREPARATION

The invention relates to new 2,7-diamino-1,2,3,4-tetrahydronaphthalenes, their preparation and their use as medicaments. The 2,7-diamino-1,2,3,4-tetrahydronaphthalenes (2,7-diaminotetralins) correspond to the general formula I

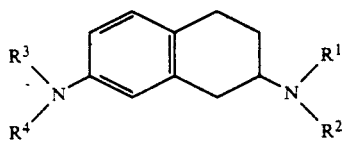

wherein
$R^1$ denotes hydrogen, $C_1$-$C_{12}$-alkyl, $(CH_2)_a$—$R^5$, $CH_2$—$CH$=$CH$—$R^6$ or alkoxycarbonyl and a is the number 1, 2, 3 or 4;
$R^2$ denotes hydrogen, $C_1$-$C_{12}$-alkyl, $(CH_2)_b$—$R^7$, allyl or $CH_2$—$CH$=$CH$—$R^8$ and b denotes the number 1, 2, 3 or 4;
$R^3$ denotes hydrogen, $C_1$-$C_{12}$-alkyl, formyl, acetyl, halogen-substituted acetyl,

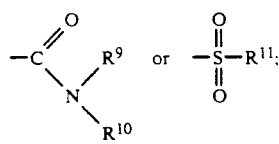

$R^4$ denotes hydrogen, $C_1$-$C_{12}$-alkyl, $C_3$-$C_{12}$-alkenyl or $C_3$-$C_{12}$-alkinyl;
$R^5$ denotes —CH=CHR$^{12}$, —C≡CHR$^{13}$, —CH$_2$—O—R$^{14}$,

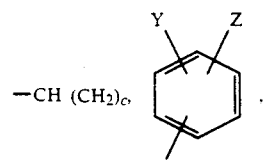

aryloxy, aralkoxy, alkylthio, arylthio, aralkylthio, aryloxycarbonyl, heteroaryl or substituted heteroaryl, such as

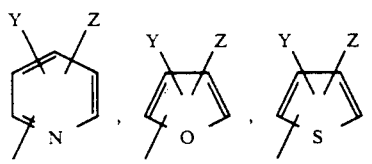

or

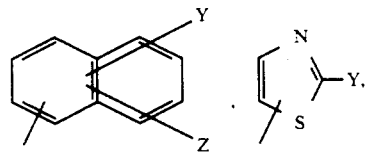

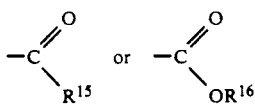

wherein
Y denotes hydrogen, halogen, lower alkyl, alkoxy, OH, NH$_2$ or NO$_2$,
Z denotes hydrogen, halogen, lower alkyl, alkoxy, OH, NH$_2$ or NO$_2$ and
c denotes the number 1, 2, 3, 4 or 5;
$R^6$ denotes

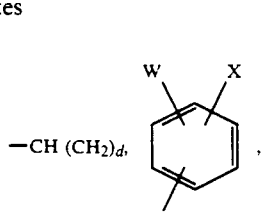

aryloxy, aralkoxy, arylthio, alkylthio, aralkylthio, aryloxycarbonyl, heteroaryl or substituted heteroaryl, such as

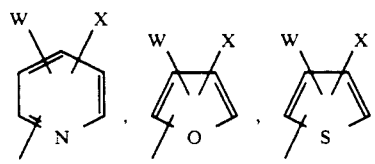

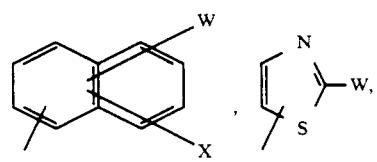

or

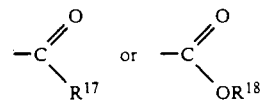

wherein
W denotes hydrogen, halogen, lower alkyl, alkoxy, OH, NH$_2$ or NO$_2$,
X denotes hydrogen, halogen, lower alkyl, alkoxy, OH, NH$_2$ or NO$_2$ and
d denotes the number 1, 2, 3, 4 or 5;
$R^7$ denotes —CH=CHR$^{19}$, —C≡CR$^{20}$, —CH$_2$—O—R$^{21}$,

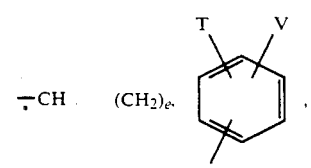

aryloxy, aralkoxy, alkylthio, arylthio, aralkylthio, aryloxycarbonyl, heteroaryl or substituted heteroaryl, such as

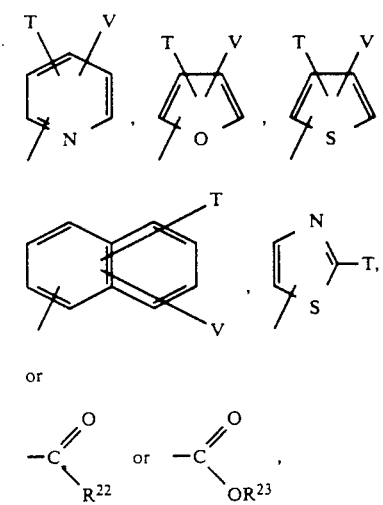

wherein
T denotes hydrogen, halogen, lower alkyl, alkoxy, OH, NH$_2$ or NO$_2$,
V denotes hydrogen, halogen, lower alkyl, alkoxy, OH, NH$_2$ or NO$_2$ and
e denotes the number 1, 2, 3, 4 or 5;
R$^8$ denotes

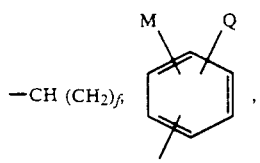

aryloxy, aralkoxy, arylthio, alkylthio, aralkylthio, aryloxycarbonyl, heteroaryl or substituted heteroaryl, such as

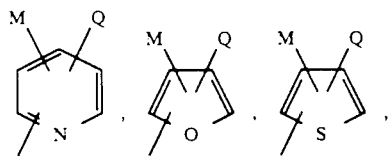

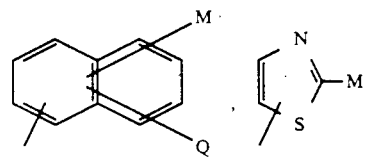

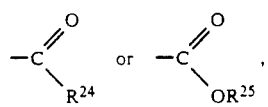

wherein
M denotes hydrogen, halogen, lower alkyl, alkoxy, OH, NH$_2$ or NO$_2$,
Q denotes hydrogen, halogen, lower alkyl, alkoxy, OH, NH$_2$ or NO$_2$ and
f denotes the number 1, 2, 3, 4 or 5;
R$^9$ denotes hydrogen or alkyl;
R$^{10}$ denotes hydrogen or alkyl; or R$^9$ and R$^{10}$, together with the nitrogen atom, can also form a heterocyclic radical which can also contain a further hetero atom—such as nitrogen, oxygen or sulfur—e.g. a morpholine, piperidine or piperazine ring;
R$^{11}$ denotes alkyl or aralkyl;
R$^{12}$ denotes hydrogen, alkyl or aryl;
R$^{13}$ denotes hydrogen or alkyl;
R$^{14}$ denotes hydrogen or alkyl;
R$^{15}$ denotes alkyl or aryl;
R$^{16}$ denotes alkyl or aryl;
R$^{17}$ denotes alkyl or aryl;
R$^{18}$ denotes alkyl or aryl;
R$^{19}$ denotes hydrogen, alkyl or aryl;
R$^{20}$ denotes hydrogen, alkyl or aryl;
R$^{21}$ denotes hydrogen or alkyl;
R$^{22}$ denotes alkyl or aryl;
R$^{23}$ denotes alkyl or aryl;
R$^{24}$ denotes alkyl or aryl and
R$^{25}$ denotes alkyl or aryl;
wherein R$^1$, R$^2$, R$^3$ and R$^4$ may not all denote hydrogen together and—in the case where R$^3$ and R$^4$ both denote hydrogen or R$^3$ denotes acetyl and R$^4$ denotes hydrogen—R$^1$ and R$^2$ may not both denote methyl or may not both denote propyl.

Preferred compounds of the general formula I are those wherein
R$^1$ denotes hydrogen, C$_1$-C$_6$-alkyl, (CH$_2$)$_2$—R$^5$, CH$_2$—CH=CH—R$^6$ or
a denotes the number 1, 2, 3 or 4;
R$^2$ denotes hydrogen, C$_1$-C$_6$-alkyl, (CH$_2$)$_b$—R$^7$, allyl or CH$_2$—CH=CH—R$^8$ and
b denotes the number 1, 2, 3 or 4;
R$^3$ denotes hydrogen, C$_1$-C$_6$-alkyl, formyl, acetyl, halogen-substituted acetyl,

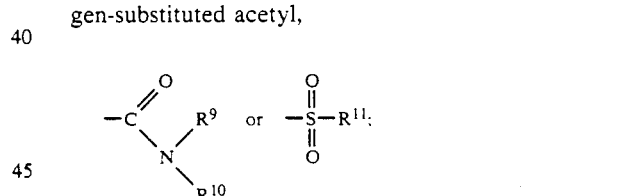

R$^4$ denotes hydrogen, C$_1$-C$_6$-alkyl, C$_3$-C$_6$-alkenyl or C$_3$-C$_6$-alkinyl;
R$^5$, R$^6$, R$^7$ and R$^8$ have the abovementioned meaning;
R$^9$ and R$^{10}$ denote hydrogen or lower alkyl, it also being possible for R$^9$ and R$^{10}$, together with the nitrogen atom, to form a 5- or 6-membered heterocyclic radical—such as e.g. a morpholine, piperidine or piperazine ring—in which a carbon atom can be replaced by a hetero atom—such as e.g. nitrogen, oxygen or sulphur; and
R$^{11}$ denotes lower alkyl or aralkyl.

Particularly preferred compounds of the general formula I are those wherein
R$^1$ denotes hydrogen, C$_1$-C$_4$-alkyl, allyl or tert.-butoxycarbonyl;
R$^2$ denotes hydrogen, C$_1$-C$_4$-alkyl, (CH$_2$)$_b$—R$^7$, allyl or CH$_2$—CH=CH—R$^8$ and
b denotes the number 1, 2, 3 or 4;
R$^3$ denotes hydrogen, formyl, acetyl, trifluoracetyl

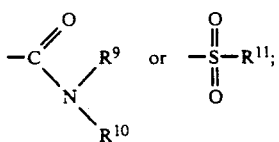

R⁴ denotes hydrogen or $C_1$-$C_4$-alkyl;
R⁷ denotes —CH=CHR¹², —C≡CR¹³, cyclopropyl, phenyl,

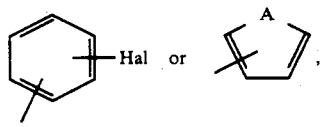

wherein Hal denotes chlorine or bromine and A denotes oxygen or sulphur;
R⁸ denotes

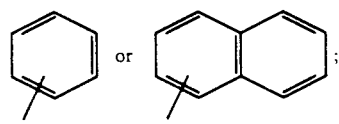

R⁹ and R¹⁰ denote hydrogen or lower alkyl;
R¹¹ denotes lower alkyl;
R¹² denotes hydrogen, lower alkyl or phenyl; and
R¹³ denotes hydrogen or lower alkyl.

The 2,7-diamino-1,2,3,4-tetrahydronaphthalenes (2,7-diaminotetralins) according to the invention have at least one C atom with a center of asymmetry and can also possess several centers of asymmetry, depending on the substitution pattern, and can therefore exist in various stereochemical forms.

The following isomers of the substituted 2,7-diaminotetralins of the general formula II and III may be mentioned as examples:

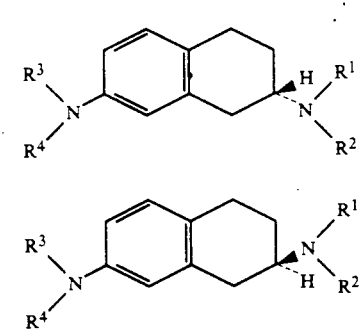

The invention relates to the individual isomers, mixtures thereof and the corresponding physiologically suitable acid addition salts with inorganic or organic acids. Preferred salts are, for example, salts with hydrochloric acid, hydrobromic acid, sulphuric acid, phosphoric acid, methanesulphonic acid, ethanesulphonic acid, toluenesulphonic acid, benzenesulphonic acid, lactic acid, malonic acid, succinic acid, maleic acid, fumaric acid, malic acid, tartaric acid, citric acid or benzoic acid.

Where no data which deviate specifically are given, the general definitions are used in the following sense:

Alkyl in general represents an unbranched or branched hydrocarbon radical with 1 to 12 carbon atoms, which can optionally be substituted by a halogen atom or several halogen atoms—preferably fluoroine—which can be identical to or different from another, lower alkyl radicals being preferred. Lower alkyl in general represents a branched or unbranched hydrocarbon radical with 1 to about 6 carbon atoms. Examples which may be mentioned are methyl, ethyl, propyl, isopropyl, butyl, isobutyl, pentyl, isopentyl, neopentyl, hexyl, isohexyl, heptyl, isoheptyl, octyl and Alkenyl in general represents a straight-chain or branched hydrocarbon radical with 3 to 12 carbon atoms and with one or more, preferably with one or two, double bond(s), which can optionally be substituted by a halogen atom or several halogen atoms—preferably fluorine—which can be identical to or different from one another. A lower alkenyl radical with 3 to about 6 carbon atoms and one or two double bond(s) is preferred. An alkenyl radical with 3 or 4 carbon atoms and one double bond is particularly preferred. Examples which may be mentioned are allyl, propenyl, isopropenyl, pentenyl, isopentenyl, hexenyl, isohexenyl, heptenyl, isoheptenyl, octenyl and isooctenyl.

Alkinyl in general represents a straight-chain or branched hydrocarbon radical with 3 to 12 carbon atoms and with one ore more, preferably with one or two, triple bond(s). A lower alkinyl radical with 3 to about 6 carbon atoms and one or two triple bond(s), which can optionally be substituted by a halogen atom or several halogen atoms—preferably fluorine—which can be identical to or different from one another if preferred. An alkinyl radical with 3 or 4 carbon atoms and one triple bond is particularly preferred. Examples which may be mentioned are propargyl and but-2-inyl.

Cycloalkyl in general represents a saturated or unsaturated cyclic hydrocarbon radical with 5 to 9 carbon atoms, which can optionally be substituted by a halogen atom or several halogen atoms—preferably fluorin—which can be identical to or different from one another. Cyclic hydrocarbon radicals with 3 to 6 carbon atoms are preferred. Examples which may be mentioned are cyclopropyl, cyclobutyl, cycloheptenyl, cycloheptadienyl, cyclooctyl, cyclooctenyl, cyclooctadienyl and cyclononinyl.

Aryl in general represents an aromatic radical with 6 to 10 carbon atoms—including in combinations, it being possible for the aromatic to be substituted by one or more lower alkyl group(s), alkoxy group(s), nitro group(s), amino group(s) and/or one or more halogen atom(s)—which are identical to or different from one another. Preferred aryl radicals are phenyl, naphthyl and biphenyl.

Aralkyl in general represents an aryl radical which has 7 to 14 carbon atoms and is bonded via an alkylene chain, it being possible for the aromatic to be substituted by one or more lower alkyl group(s), alkoxy group(s), nitro group)s), amino group(s) and/or one or more halogen atom(s)—which can be identical to or different from one another. Aralkyl radicals with 1 to 6 carbon atoms in the aliphatic part and 6 to 10 carbon atoms in the aromatic part are preferred. Preferred aralkyl radicals which may be mentioned are: benzyl, naphthyl, phenethyl and phenylpropyl.

Alkoxy in general represents a straight-chain or branched hydrocarbon radical which has 1 to 12 carbon atoms and is bonded via an oxygen atom. A lower alkoxy radical with 1 to about 6 carbon atoms is preferred.

An alkoxy radical with 1 to 4 carbon atoms is particularly preferred. Examples which may be mentioned are methoxy, ethoxy, propoxy, isopropoxy, butoxy, isobutoxy, tert.-butoxy, pentoxy, isopentoxy, hexoxy, isohexoxy, heptoxy, isoheptoxy, octoxy and isooctoxy.

Aryloxy in general represents an aromatic radical with 6 to about 12 carbon atoms which is bonded via an oxygen atom and can optionally be substituted by one or more lower alkyl group(s), alkoxy group(s), nitro group(s), amino group(s) and/or halogen atom(s)—which are identical to or different from one another. Preferred aryloxy radicals are phenoxy or naphthyloxy.

Aralkoxy in general represents an aralkyl radical with 7 to 14 carbon atoms, the alkylene chain being bonded via an oxygen atom. Arylkoxy radicals with 1 to 6 carbon atoms in the aliphatic part and 6 to 10 carbon atoms in the aromatic part are preferred. The following aralkoxy radicals may be mentioned as examples: benzyloxy, naphthmethyloxy, phenethoxy and phenylpropoxy.

Alkylthio in general represents a straight-chain or branched hydrocarbon radical which has 1 to 12 carbon atoms and is bonded via a sulphur atom. Lower alkylthios with 1 to 6 carbon atoms is preferred. An alkylthio radical with 1 to 4 carbon atoms is particularly preferred. Examples which may be mentioned are methylthio, ethylthio, propylthio, isopropylthio, butylthio, isobutylthio, hexylthio, isohexylthio, heptylthio, isoheptylthio, octylthio and isooctylthio.

Arylthio in general represents an aromatic radical which has 6 to about 12 carbon atoms and is bonded via a sulphur atom, and can optionally be substituted by one or more lower alkyl group(s), alkoxy group(s), nitro group(s), amino group(s) and/or halogen atom(s)—which are identical to or different from one another. Examples which may be mentioned are the phenylthio and the naphthylthio radical, the phenylthio radical being preferred.

Aralkylthio in general represents an aralkyl radical with 7 to 14 carbon atoms, the alkylene chain being bonded via a sulphur atom. Aralkylthio radicals with 1 to 6 carbon atoms in the aliphatic part and with 6 to 12 carbon atoms in the aromatic part are preferred, it being possible for both the aliphatic and the aromatic part to be substituted by one ore more lower alkyl group(s), alkoxy group(s), nitro group(s), amino group(s) and/or halogen atom(s)—which are identical to or different from one another. Examples which may be mentioned are the benzylthio and the phenylthio radical.

Acyl in general represents benzoyl, or represents an alkylcarbonyl radical—such as straight-chain or branched lower alkyl with 1 to about 6 carbon atoms—which is bonded via a carbonyl group, it being possible for the alkyl radical to be optionally substituted by one or more halogen atom(s), which can identical to or different from one another. Alkyl radicals with up to 4 carbon atoms are preferred. Examples which may be mentioned are: benzyl, acetyl, ethylcarbonyl, propylcarbonyl, isopropylcarbonyl, butylcarbonyl and isobutylcarbonyl.

Alkoxycarbonyl can be represented, for example, by the formula

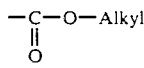

Alkyl here represents a straight-chain or branched hydrocarbon radical with 1 to 12 carbon atoms. A lower alkyoxycarbonyl radical with 1 to 6 carbon atoms is preferred. An alkoxycarbonyl radical with 1 to 4 carbon atoms in the alkyl radical is particularly preferred. The following alkoxycarbonyl radicals may be mentioned as examples: methoxycarbonyl, ethoxycarbonyl, propoxycarbonyl, isopropoxycarbonyl, butoxycarbonyl and isobutoxycarbonyl.

Aryloxycarbonyl can be represented by the formula

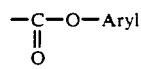

Aryl here in general represents an aromatic radical with 6 to 12 carbon atoms—for example: phenoxycarbonyl or naphthyloxycarbonyl.

Aralkoxycarbonyl can be represented by the formula

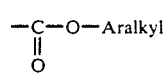

Aralkyl here represents an aryl radical which has 7 to 14 carbon atoms and is bonded via an alkylene chain; aralkyl radicals with 1 to 6 carbon atoms in the aliphatic part and 6 to 12 carbon atoms in the aromatic part are preferred. Examples of aralkoxycarbonyl radicals which may be mentioned are benzyloxycarbonyl and naphthylmethyloxycarbonyl.

Heteroaryl in the context of the definition given above in general represents a 5- to 6-membered ring which can contain oxygen, sulphur and/or nitrogen as hetero atoms and onto which a further aromatic ring can be fused. 5- and 6-membered aromatic rings which contain one oxygen, one sulphur and/or up to two nitrogen atoms and which are optionally benzo-fused are preferred. Examples of particular heteroaryl radicals which may be mentioned are thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benzoxazolyl, isoxazolyl, imidazlyl, benzimidazolyl, pyrazolyl and indolyl.

The preferred meaning for $R^1$ is hydrogen, methyl, ethyl, propyl, butyl or allyl.

The preferred meaning for $R^2$ is propyl, butyl, cyclopropylmethyl, allyl, propargyl, phenethyl, 3-phenylpropyl, 4-phenylbutyl, 3-phenylpropargyl, 2-(2-thienyl)ethyl, 2-(3-thienyl)ethyl, 2-(4-chlorphenyl)ethyl or 3-(4-chlorophenyl)propyl.

The preferred meaning for $R^3$ is formyl, acetyl or halogen-substituted acetyl.

The preferred meaning for $R^4$ is hydrogen.

Halogen denotes—unless stated otherwise—chlorine or bromine, and in addition also fluorine and in second place iodine.

The following compounds may be mentioned as examples:

7-acetamido-2-methylamino-1,2,3,4-tetrahydronaphthalene 7-acetamido-2-ethylamino-1,2,3,4-tetrahydronaphthalene 7-acetamido-2-propylamino-1,2,3,4-tetrahydronaphthalene 7-acetamido-2-[2-(2-thienyl)ethyl]amino-1.2,3,4-tetrahydronaphthalene 7-acetamido-2-[2-(3-thienyl)ethyl]amino-1,2,3,4-tetrahydronaphthalene
7-acetamido-2-N,N-dibutylamino-1,2,3,4-tetrahydronaphthalene
7-acetamido-2-(N-butyl-N-propyl)amino-1,2,3,4-tetrahydronaphthalene
7-acetamido-2-[N-2-(2-thienyl)ethyl)-N-propyl]amino-1,2,3,4-tetrahydronaphthalene
7-acetamido-2-[N-2-(3-thienyl)ethyl)-N-propyl]amino-1,2,3,4-tetrahydronaphthalene
7-acetamido-2-(N-benzyl-N-propyl)amino-1,2,3,4-tetrahydronaphthalene
7-acetamido-2-(N-phenylethyl-N-propyl)amino-1,2,3,4-tetrahydronaphthalene
7-acetamido-2-[N-(3-phenylpropyl-N-propyl]amino-1,2,3,4-tetrahydronaphthalene
7-acetamido-2-(N-allyl-N-propyl)amino-1,2,3,4-tetrahydronaphthalene
7-acetamido-2-(3-phenylallyl)amino-1,2,3,4-tetrahydronaphthalene
7-acetamido-2-[N-(3-phenylallyl)-N-propyl]amino-1,2,3,4-tetrahydronaphthalene
7-acetamido-2-N,N-diallylamino-1,2,3,4-tetrahydronaphthalene
7-acetamido-2-(N-propargyl-N-propyl)amino-1,2,3,4-tetrahydronaphthalene
7-acetamido-2-[N-(4-phenylbutyl)-N-propyl]amino-1,2,3,4-tetrahydronaphthalene
7-acetamido-2-[N-2-(4-chlorphenyl)ethyl-N-propyl]amino-1,2,3,4-tetrahydronaphthalene
7-acetamido-2-(N-isopropyl-N-propyl)amino-1,2,3,4-tetrahydronaphthalene
7-acetamido-2-(N-cyclopropylmethyl-N-propyl)amino-1,2,3,4-tetrahydronaphthalene
7-acetamido-2-N,N-di(3-phenylpropyl)amino-1,2,3,4-tetrahydronaphthalene
7-acetamido-2-<N-[3-(4chlorophenyl)propyl]-N-propyl>amino-1,2,3,4-tetrahydronaphthalene
7-acetamido-2-(N-methyl-N-propyl)amino-1,2,3,4-tetrahydronaphthalene
(−)-7-acetamido-2-(N-butyl-N-propyl)amino-1,2,3,4-tetrahydronaphthalene
(+)-7-acetamido-2-(N-butyl-N-propyl)amino-1,2,3,4-tetrahydronaphthalene
(−)-7-acetamido-2-(N-pentyl-N-propyl)amino-1,2,3,4-tetrahydronaphthalene
(+)-7-acetamido-2-(N-pentyl-N-propyl)amino-1,2,3,4-tetrahydronaphthalene
(−)-7-acetamido-2-(N-methyl-N-phenethyl)amino-1,2,3,4-tetrahydronaphthalene
(+)-7-acetamido-2-(N-methyl-N-phenethyl)amino-1,2,3,4-tetrahydronaphthalene
(−)-7-acetamido-2-[N-(3-phenylpropyl)-N-propyl]amino-1,2,3,4-tetrahydronaphthalene
(+)-7-acetamido-2-[N-(3-phenylpropyl)-N-propyl]amino-1,2,3,4-tetrahydronaphthalene
(−)-7-acetamido-2-[N-(3-phenylallyl)-N-propyl]amino-1,2,3,4-tetrahydronaphthalene
(+)-7-acetamido-2-[N-(3-phenylallyl)-N-propyl]amino-1,2,3,4-tetrahydronaphthalene
(−)-7-acetamido-2-[N-(2-methoxyethyl)-N-propyl]amino-1,2,3,4-tetrahydronaphthalene
(+)-7-acetamido-2-[N-(2-methoxyethyl)-N-propyl]amino-1,2,3,4-tetrahydronaphthalene
(−)-7-acetamido-2-[N-(2-phenoxyethyl)-N-propyl]amino-1,2,3,4-tetrahydronaphthalene
(+)-7-acetamido-2-[N-(2-phenoxyethyl)-N-propyl]amino-1,2,3,4-tetrahydronaphthalene
(−)-7-acetamido-2-[N-(2-benzyloxyethyl)-N-propyl]amino-1,2,3,4-tetrahydronaphthalene
(+)-7-acetamido-2-[N-(2-benzyloxyethyl)-N-propyl]amino-1,2,3,4-tetrahydronaphthalene
(−)-7-acetamido-2-[N-(3-methoxypropyl)-N-propyl]amino-1,2,3,4-tetrahydronaphthalene
(+)-7-acetamido-2-[N-(3-methoxypropyl)-N-propyl]amino-1,2,3,4-tetrahydronaphthalene
(−)-7-acetamido-2-[N-(2-methylthioethyl)-N-propyl]amino-1,2,3,4-tetrahydronaphthalene
(+)-7-acetamido-2-[N-(2-methylthioethyl)-N-propyl]amino-1,2,3,4-tetrahydronaphthalene
(−)-7-acetamido-2-[N-(2-phenylthioethyl)-N-propyl]amino-1,2,3,4-tetrahydronaphthalene
(+)-7-acetamido-2-[N-(2-phenylthioethyl)-N-propyl]amino-1,2,3,4-tetrahydronaphthalene
(−)-7-acetamido-2-[N-(3-methylthiopropyl)-N-propyl]amino-1,2,3,4-tetrahydronaphthalene
(+)-7-acetamido-2-[N-(3-methylthiopropyl)-N-propyl]amino-1,2,3,4-tetrahydronaphthalene
(−)-7-acetamido-2-[N-(but-3-enyl)-N-propyl]amino-1,2,3,4-tetrahydronaphthalene
(+)-7-acetamido-2-[N-(but-3-enyl)-N-propyl]amino-1,2,3,4-tetrahydronaphthalene
(−)-7-acetamido-2-[N-(2-methoxycarbonylethyl)-N-propyl]amino-1,2,3,4-tetrahydronaphthalene
(+)-7-acetamido-2-[N-(2-methoxycarbonylethyl)-N-propyl]amino-1,2,3,4-tetrahydronaphthalene
(−)-7-acetamido-2-[N-(2-phenoxycarbonylethyl)-N-propyl]amino-1,2,3,4-tetrahydronaphthalene
(+)-7-acetamido-2-[N-(2-methoxycarbonylethyl)-N-propyl]amino-1,2,3,4-tetrahydronaphthalene
(−)-7-acetamido-2-[N-(2-hyddroxycarbonylethyl)-N-propyl]amino-1,2,3,4-tetrahydronaphthalene
(+)-7-acetamido-2-[N-(2-hyddroxycarbonylethyl)-N-propyl]amino-1,2,3,4-tetrahydronaphthalene
(−)-7-acetamido-2-[N-(3-oxo-butyl)-N-propyl]amino-1,2,3,4-tetrahydronaphthalene
(+)-7-acetamido-2-[N-(3-oxo-butyl)-N-propyl]amino-1,2,3,4-tetrahydronaphthalene
(−)-7-acetamido-2-<N-[2-(2-furyl)ethyl]-N-propyl>amino-1,2,3,4-tetrahydronaphthalene
(+)-7-acetamido-2-<N-[2-(2-furyl)ethyl]-N-propyl>amino-1,2,3,4-tetrahydronaphthalene
(−)-7-acetamido-2-<N-propyl-N-[2-(2-pyridyl)ethyl]->amino-1,2,3,4-tetrahydronaphthalene
(+)-7-acetamido-2-<N-propyl-N-[2-(2-pyridyl)ethyl]->amino-1,2,3,4-tetrahydronaphthalene
(−)-7-acetamido-2-<N-propyl-N-[2-(3-pyridyl)ethyl]->amino-1,2,3,4-tetrahydronaphthalene
(+)-7-acetamido-2-<N-propyl-N-[2-(3-pyridyl)ethyl]->amino-1,2,3,4-tetrahydronaphthalene
(−)-7-acetamido-2-<N-propyl-N-[2-(4-pyridyl)ethyl]->amino-1,2,3,4-tetrahydronaphthalene
(+)-7-acetamido-2-<N-propyl-N-[2-(4-pyridyl)ethyl]->amino-1,2,3,4-tetrahydronaphthalene
(−)-7-acetamido-2-<N-[2-(4-methoxyphenyl)ethyl]-N-propyl>amino-1,2,3,4-tetrahydronaphthalene
(+)-7-acetamido-2-<N-[2-(4-methoxyphenyl)ethyl]-N-propyl>amino-1,2,3,4-tetrahydronaphthalene
(−)-7-acetamido-2-<N-[2-(4-methylphenyl)ethyl]-N-propyl>amino-1,2,3,4-tetrahydronaphthalene
(+)-7-acetamido-2-<N-[2-(4-methylphenyl)ethyl]-N-propyl>amino-1,2,3,4-tetrahydronaphthalene
(−)-7-acetamido-2-<N-[2-(4-hydroxyphenyl)ethyl]-N-propyl>amino-1,2,3,4-tetrahydronaphthalene
(+)-7-acetamido-2-<N-[2-(4-hydroxyphenyl)ethyl]-N-propyl>amino-1,2,3,4-tetrahydronaphthalene (−)-7-acetamido-2-<N-[2-(3,4-dimethoxyphenyl)ethyl]-N-propyl>amino-1,2,3,4-tetrahydronaphthalene
(+)-7-acetamido-2-<N-[2-(3,4-dimethoxyphenyl)ethyl]-N-propyl>amino-1,2,3,4-tetrahydronaphthalene
(−)-7-acetamido-2-<N-[2-(3-chlorophenyl)ethyl]-N-propyl>amino-1,2,3,4-tetrahydronaphthalene
(+)-7-acetamido-2-<N-[2-(3-chlorophenyl)ethyl]-N-propyl>amino-1,2,3,4-tetrahydronaphthalene
(−)-7-acetamido-2-<N-[2-(3,4-dichlorophenyl)ethyl]-N-propyl>amino-1,2,3,4-tetrahydronaphthalene
(+)-7-acetamido-2-<N-[2-(3,4-dichlorophenyl)ethyl]-N-propyl>amino-1,2,3,4-tetrahydronaphthalene
(−)-7-acetamido-2-<N-[2-(3,5-dichlorophenyl)ethyl]-N-propyl>amino-1,2,3,4-tetrahydronaphthalene
(+)-7-acetamido-2-<N-[2-(3,5-dichlorophenyl)ethyl]-N-propyl>amino-1,2,3,4-tetrahydronaphthalene
(−)-7-acetamido-2-<N-[2-(1-naphthyl)ethyl]-N-propyl>amino-1,2,3,4-tetrahydronaphthalene
(+)-7-acetamido-2-<N-[2-(1-naphthyl)ethyl]-N-propyl>amino-1,2,3,4-tetrahydronaphthalene
(−)-7-acetamido-2-<N-[2-(2-naphthyl)ethyl]-N-propyl>amino-1,2,3,4-tetrahydronaphthalene
(+)-7-acetamido-2-<N-[2-(2-naphthyl)ethyl]-N-propyl>amino-1,2,3,4-tetrahydronaphthalene
(−)-7-acetamido-2-[N-(2-phenylpropyl)-N-propyl]amino-1,2,3,4-tetrahydronaphthalene
(+)-7-acetamido-2-[N-(2-phenylpropyl)-N-propyl]amino-1,2,3,4-tetrahydronaphthalene
(−)-7-acetamido-2-[N-(2-cyclohexylethyl)-N-propyl]amino-1,2,3,4-tetrahydronaphthalene
(+)-7-acetamido-2-[N-(2-cyclohexylethyl)-N-propyl]amino-1,2,3,4-tetrahydronaphthalene
(−)-7-acetamido-2<N-propyl-N-[3-(2-pyridylallyl]->amino-1,2,3,4-tetrahydronaphthalene
(+)-7-acetamido-2<N-propyl-N-[3-(2-pyridylallyl]->amino-1,2,3,4-tetrahydronaphthalene
7-amino-2-methylamino-1,2,3,4-tetrahydronaphthalene
7-amino-2-ethylamino-1,2,3,4-tetrahydronaphthalene
7-amino-2-propylamino-1,2,3,4-tetrahydronaphthalene
7-amino-2-benzylamino-1,2,3,4-tetrahydronaphthalene
7-amino-2-[2-(2-thienyl)ethyl]amino-1,2,3,4-tetrahydronaphthalene
7-amino-2-[2-(3-thienyl)ethyl]amino-1,2,3,4-tetrahydronaphthalene
7-amino-2-N,N-dimethylamino-1,2,3,4-tetrahydronaphthalene
7-amino-2-N,N-diethylamino-1,2,3,4-tetrahydronaphthalene
7-amino-2-N,N-dipropylamino-1,2,3,4-tetrahydronaphthalene
7-amino-2-N,N-dibutylamino-1,2,3,4-tetrahydronaphthalene
7-amino-2-(N-methyl-N-propyl)amino-1,2,3,4-tetrahydronaphthalene
7-amino-2-(N-butyl-N-propyl)amino-1,2,3,4-tetrahydronaphthalene
7-amino-2-(N-benzyl-N-methyl)amino-1,2,3,4-tetrahydronaphthalene
7-amino-2-(N-benzyl-N-ethyl)amino-1,2,3,4-tetrahydronaphthalene
7-amino-2-(N-benzyl-N-propyl)amino-1,2,3,4-tetrahydronaphthalene
7-amino-2-(N-phenylethyl-N-propyl)amino-1,2,3,4-tetrahydronaphthalene
7-amino-2-(N-methyl-N-phenethyl)amino-1,2,3,4-tetrahydronaphthalene
7-amino-2-[N-(3-phenylpropyl-N-propyl]amino-1,2,3,4-tetrahydronaphthalene
2-(N-allyl-N-methyl)amino-7-amino-1,2,3,4-tetrahydronaphthalene
2-(N-allyl-N-ethyl)amino-7-amino-1,2,3,4-tetrahydronaphthalene
2-(N-allyl-N-propyl)amino-7-amino-1,2,3,4-tetrahydronaphthalene
7-amino-2-N,N-diallyl-1,2,3,4-tetrahydronaphthalene
7-amino-2-(N-propargyl-N-propyl)amino-1,2,3,4-tetrahydronaphthalene
7-amino-2-N,N-dipropargylamino-1,2,3,4-tetrahydronaphthalene
7-amino-2-[N-(4-phenylbutyl)-N-propyl]amino-1,2,3,4-tetrahydronaphthalene
7-amino-2-<N-[2-(4-chlorophenyl)ethyl]-N-propyl>amino-1,2,3,4-tetrahydronaphthalene
7-amino-2-[N-ethyl-N-(2-pyridyl)methyl]amino-1,2,3,4-tetrahydronaphthalene
7-amino-2-<N-propyl-N-[(2-thienyl)methyl]>amino-1,2,3,4-tetrahydronaphthalene
7-amino-2-<N-propyl-N-[(3-thienyl)methyl]>amino-1,2,3,4-tetrahydronaphthalene
7-amino-2-<N-propyl-N-[2(2-thienyl)ethyl]>amino-1,2,3,4-tetrahydronaphthalene
7-amino-2-<N-propyl-N-[2-(3-thienyl)ethyl]>amino-1,2,3,4-tetrahydronaphthalene
7-amino-2-(N-cyclopropylmethyl-N-propyl)amino-1,2,3,4-tetrahydronaphthalene
7-amino-2-[N-(3-phenyl)allyl-N-propyl]amino-1,2,3,4-tetrahydronaphthalene
7-amino-2-[N-(3-phenylpropargyl)-N-propyl]amino-1,2,3,4-tetrahydronaphthalene
7-amino-2-N,N-di(3-phenylpropyl)amino-1,2,3,4-tetrahydronaphthalene
(−)-7-amino-2-(N-butyl-N-propyl)amino-1,2,3,4-tetrahydronaphthalene
(+)-7-amino-2-(N-butyl-N-propyl)amino-1,2,3,4-tetrahydronaphthalene
(−)-7-amino-2-(N-phenylethyl-N-propyl)amino-1,2,3,4-tetrahydronaphthalene
(+)-7-amino-2-(N-phenylethyl-N-propyl)amino-1,2,3,4-tetrahydronaphthalene
(−)-7-amino-2-[N-(3-phenylpropyl)-N-propyl]amino-1,2,3,4-tetrahydronaphthalene
(+)-7-amino-[N-(3-phenylpropyl)-N-propyl]amino-1,2,3,4-tetrahydronaphthalene
(−)-7-amino-[N-(3-phenylallyl)-N-propyl]amino-1,2,3,4-tetrahydronaphthalene
(+)-7-amino-2-[N-(3-phenylallyl)-N-propyl]amino-1,2,3,4-tetrahydronaphthalene
7-dimethylamino-2-dipropylamino-1,2,3,4-tetrahydronaphthalene
2-dipropylamino-7-methylamino-1,2,3,4-tetrahydronaphthalene
7-dimethylamino-2-(N-phenethyl-N-propyl)amino-1,2,3,4-tetrahydronaphthalene
7-methylamino-2-(N-phenylethyl-N-propyl)amino-1,2,3,4-tetrahydronaphthalene
7-amino-2-tert.-butoxycarbonylamido-1,2,3,4-tetrahydronaphthalene
7-acetamido-2-tert.-butoxycarbonylamido-1,2,3,4-tetrahydronaphthalene
7acetamido-2-amino-1,2,3,4-tetrahydronaphthalene
7acetamido-2(3-phenylallyl)amino-1,2,3,4-tetrahydronaphthalene
7acetamido-2-benzylamino-1,2,3,4-tetrahydronaphthalene 7acetamido-2N,N-diethylamino-1,2,3,4-tetrahydronaphthalene 7acetamido-2(N-allyl-N-methyl)amino-1,2,3,4-tetrahydronaphthalene 7acetamido-2[N-methyl-N-(3phenylallyl)]amino-1,2,3,4-tetrahydronaphthalene 7amino-2-ethylamino-1,2,3,4-tetrahydronaphthalene 2dipropylamino-7-methanesulphonamido-1,2,3,4-tetrahydronaphthalene 2-(N-phenethyl-N-propyl)amino-7-trifluoroacetamido-1,2,3,4-tetrahydronaphthalene 7-formamido-2-(N-phenethyl-N-propyl)amino-1,2,3,4-tetrahydronaphthalene 7-carboylamido-2-dipropylamino-1,2,3,4-tetrahydronaphthalene 2-dipropylamino-7-(N-methyl-formamido)-1,2,3,4-tetrahydronaphthalene 2-dipropylamino-7-(N-methyl-acetamido)-1,2,3,4-tetrahydronaphthalene 2-dipropylamino-7-ethylamino-1,2,3,4-tetrahydronaphthalene 7-acetamido-2-methylamino-1,2,3,4-tetrahydronaphthalene 7-(N-methyl-acetamido)-2-(N-phenylethyl-N-propyl)amino-1,2,3,4-tetrahydronaphthalene 2-N,N-dipropylamino-7-(N-propyl-acetamido)-1,2,3,4-tetrahydronaphthalene The new compounds and their physiologically acceptable acid addition salts have useful pharmacological properties and show actions on the blood pressure and heart rate and on prolactin secretion, and in particular on the central nervous system. The compounds according to the invention exhibit a presynaptic dopamine-agnostic action with a simultaneous absence of a postsynaptic dopaminergic action. On the basis of these properties, the side effects of the antipsychotic agents (neuroleptics) employed to date are not to be expected. This novel action profile makes the compounds according to the invention particularly suitable for the treatment of schizophrenia.

Compounds which have proved to be useful here are the compounds and hydrochlorides of the general formula I in which $R^1$ denotes hydrogen, methyl, ethyl, propyl, butyl or allyl, $R^2$ denotes an alkyl radical—such as propyl or butyl—or an alkenyl radical—such as allyl—or an alkinyl radical—such as propargyl—or an aralkyl radical—such as phenethyl or thienylethyl—$R^3$ denotes an acetyl or halogen-substituted acetyl group and $R^4$ denotes hydrogen or lower alkyl.

Examples which have proved to be particularly useful are:

A: 7acetamido-2-<N-propyl-N-[2-(3-thienyl)ethyl]->amino-1,2,3,4-tetrahydronaphthalene hydrochloride B: 7acetamido-2-(N-butyl-N-propyl)amino-1,2,3,4-tetrahydronaphthalene hydrochloride C: 7acetamido-2-(N-allyl-N-propyl)amino-1,2,3,4-tetrahydronaphthalene hydrochloride D: 7acetamido-2-(N-phenylethyl-N-propyl)amino-1,2,3,4-tetrahydronaphthalene hydrochloride E: 7acetamido-2-(N-pentyl-N-propyl)amino-1,2,3,4-tetrahydronaphthalene hydrochloride F: 7acetamido-2-(N-propargyl-N-propyl)amino-1,2,3,4-tetrahydronaphthalene hydrochloride (In the following tables, instead of the compound names, the letters allocated to these—if appropriate, supplemented by information on the optical isomer (+) or (−)—are used.

To investigate the influencing of presynaptically dopaminergic receptors, the action on the exploratory activity of mice and the inhibition of dopamine synthesis were determined. The action on postsynaptic dopamine receptors was determined on monkeys (MPTP model) and on 6-OHDA-damaged rats.

Inhibition of the Night-Time Motility of Mice

The motility of individual female mice of the strain ChbI:NMR (SPF) (weight 20 g) is measured in cages ($42 \times 24 \times 15$ cm) with horizontal light barriers. All the interruptions in the light barriers are recorded at hourly intervals with on-line detection by computer over the 14 hours of one night. The substance is administered subcutaneously in 0.9 percent NaCl solution immediately before the start of measurement. Placebo-treated control animals are investigated in parallel with the animals treated with substance. On evaluation, the mean value and the standard deviation are determined from the results of in each case 5 animals per treatment group.

The results are summarized in the following table:

TABLE 1

| | Inhibition of night-time motility | | |
|---|---|---|---|
| Substance | Dose range investigated (mg/kg s.c) | First effective dose (mg/kg s.c) | Action time after administration (h) |
| B | 0.1–10 | 1.0 | 0–8 |
| C | 0.1–10 | 10.0 | 0–3 |
| (+)–C | 0.1–10 | 10.0 | 0–3 |
| C | 0.1–10 | 10.0 | 0–7 |
| (+)–D | 0.1–10 | 10.0 | 0–7 |
| E | 0.1–10 | 10.0 | 0–4 |
| F | 0.1–10 | 10.0 | 0–5 |

Determination of Dopamine Synthesis Inhibition

The method is performed in accordance with J. R. Walters and R. H. Roth [Naunyn—Schmiedeberg's Arch. Pharmacol. 296, (1976) 5]: For this, 5 animals are each given 10 mg/kg s.c. substance under investigation. After 5 minutes, 750 mg/kg i.p. γ-butyrolactone are administered in order to exclude the influence of postsynaptic recoupling loops on the dopamine synthesis rate via blockade of the presynaptic pulse conduction. The administration of γ-butyrolactone leads to a considerable increase in DOPA or dopamine synthesis. To inhibit the decarboxylation of DOPA, 200 mg/kg i.p. 3-hydroxybenzyl-hydrazine hydrochloride are administered after a further 5 minutes. 40 minutes after administration of the substance the animals are sacrificed and the corpus striatum exposed. Measurement of the DOPA content is with the aid of HPLC with electrochemical detection (standard: dihydroxybenzylamine).

The percentage inhibition of γ-butyrolactone-stimulated dopa accumulation effected by the test substance is determined in comparison with the control animals treated with 0.9 percent sodium chloride solution.

The results of this experiment are summarized in the following table:

TABLE 2

| Substance | Dose (mg/kg s.c.) | Inhibition of the dopa accumulation in % compared with the control animals treated with sodium chloride |
|---|---|---|
| A | 10 | 79 |
| B | 10 | 82 |
| (+)–B | 10 | 89 |

TABLE 2-continued

| Substance | Dose (mg/kg s.c.) | Inhibition of the dopa accumulation in % compared with the control animals treated with sodium chloride |
|---|---|---|
| (−)−B | 10 | 47 |
| C | 10 | 63 |
| (+)−C | 10 | 71 |
| D | 10 | 73 |
| (+)−D | 10 | 68 |
| (−)−D | 10 | 34 |
| E | 10 | 87 |
| F | 10 | 60 |

Determination of the Postsynaptic Dopaminergic Action by Means of the MPTP Model The pharmacological properties of the neurotoxin 1-methyl-4-phenyl-1,2,5,6-tetrahydro-pyridine (MPTP) [J. W. Langston, P. Bollard, J. W. Tetrud and I. Irwin, Science 219, (1983) 979] enables it to be used in the animal model for Parkinson's disease.

The irreversible neurological syndrome induced by MPTP in humans and in monkeys is largely similar in its clinical, pathological, biochemical and pharmacological manifestation to the idiopathic Parkinson'disease [S. D. Markey, J. N. Johannessen, C. C. Chivek, R. S. Burns and M. A. Herkenham, Nature 311, (1984) 464]. The reason for this convincing agreement is the fact that MPTP selectively destroys small groups of dopaminergic nerve cells in the substantial nigra of the brain, and these are also destroyed by degenerative processes during naturally occurring Parkinson's disease.

There is the possibility that the cause of idiopathic Parkinson's disease is MPTP formed in the organism or a similar chemical compound [S. H. Snyder, Nature 311 (1984) 514]. The clinical manifestation of the MPTP Parkinson's syndrome was—possibly because of the specific metabolism of the MPTP—previously detectably only in monkeys, apart from in humans.

The MPTP model realized in rhesus monkeys is therefore suitable for testing the action of postsynaptically dopamine-agnostic substances.

For this, rhesus monkeys are given MPTP in total doses of up to about 6 mg/kg body weight until the following symptoms occur: the animals become akinetic and are not capable of taking in water and food. They exhibit a typical bent attitude; cataleptic states occasionally occur. The extremities exhibit a rigor which is interspersed with clonic spasms on passive movement. Dopamine agonists, such as B-HT 920, levadopa or apomorphine, lead to a temporary removal of this syndrome for the period from 4 to 5 hours under a single dose of 100 μg/kg intramuscularly. Thereafter, the symptoms described above occur again.

After intramuscular administration of the compounds according to the invention (0.1–3.0 mg/kg), no improvement or even removal of the syndrome of monkeys treated with MPTP can be observed. With some of the compounds according to the invention, an antagonizing of the B-HT 920-caused removal of the Parkinson-like symptoms is observed. The animals remain bradykinetic on administration of 1.00–3.0 mg/kg of the compounds according to the invention together with 0.1 mg/kg B-HT 920, and continue to be unable to take in water and food. A postsynaptic dopamine-antagonistic action of these substances is to be concluded from this.

The results are summarized in the following table:

TABLE 3

| Substance | Dose | Action |
|---|---|---|
| A | up to 2 mg/kg | no removal of the MPTP symptoms |
| B | 3 mg/kg | antagonizing of B-HT 920* |
| (+)−B | 0.6 mg/kg | antagonizing of B-HT 920* |
| (−)−B | 2 mg/kg | antagonizing of B-HT 920* |
| C | 3 mg/kg | antagonizing of B-HT 920* |
| (+)−C | 1 mg/kg | antagonizing of B-HT 920* |
| D | 1 mg/kg | antagonizing of B-HT 920* |
| (+)−D | 0.5 mg/kg | antagonizing of B-HT 920* |
| E | 3 mg/kg | antagonizing of B-HT 920* |
| F | 1 mg/kg | antagonizing of B-HT 920* |

*0.1 mg B-HT 920 per kg body weight.

Determination of the Postsynaptic Dopaminergic Action by Means of 6-OH-Dopamine-(OHDA)-Damaged Rats The nigrostriatal path is interrupted in rats by injection of 6-OHDA into the medial prosencephalic bundle. Successfully damaged rats are selected by test doses of apomorphine. The rotational behaviour is determined by a modified rotameter in accordance with the method of Ungerstedt and Arbuthnott [Brain Res. 24, (1970) 485], the percentage reduction, caused by the test substance, in contralateral rotations caused by administration of 0.1 mg/kg B-HT 920 being measured.

The results are summarized in the following table:

TABLE 4

| Substance | Dose mg/kg | Reduction in the rotations in the period 15′–30′ and 60′–75′ after substance administration | |
|---|---|---|---|
| B | 3 | 22% | 95% |
| (+)−B | 3 | 93% | 99% |
| C | 3 | 86% | 93% |
| (+)−C | 1 | 71% | 49% |
| D | 3 | 100% | 82% |
| (+)−D | 1 | 43% | 76% |
| (−)−D | 3 | 47% | 73% |
| F | 3 | 43% | 36% |

I

The 2,7-diamino-1,2,3,4-tetrahydronaphthalene used as the starting material can be prepared by known methods [S. Chiavarelli and G. Settimj, Rend. ist. super. sanita 22 (1959) 508; C.A. 54 (1960) 2281 g] and resolved into the two enantiomers by the customary methods—for example via the corresponding tartaric acid salts.

II

The protection of the amino function ($R_5$) needed for the further synthesis can be achieved using the methods known from the prior art [M. Bodanszky, Principles of Peptide Synthesis, Springer-Verlag, Berlin 1984, p. 84; T. W. Greene, Protective Groups in Organic Synthesis, John Wiley and Sons, New York 1981, p. 218 et seq.; Houben-Weyl, Methoden der organischen Chemie (Methods of Organic Chemistry), volume E4, Georg Thieme Verlag, Stuttgart 1983, p. 144], protection of the amino function with an alkoxycarbonyl or an aryloxycarbonyl protective group being preferred and the tert.-butoxycarbonyl (BOC) protective group being particularly preferred.

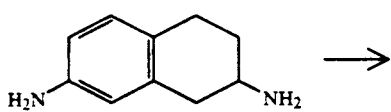

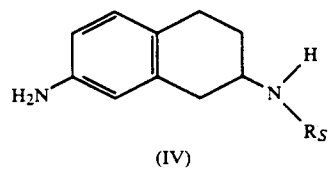

Thus, for example, using methods which are known per se—with di-tert.-butyl pyrocarbonate in the presence of a basic compound—preferably an organic nitrogen base, such as e.g. triethylamine, in inert solvents—the corresponding enantiomerically pure 7-amino-2-tert.-butoxycarbonylamido-1,2,3,4-tetrahydronaphthalene can be prepared. Organic solvent which do not change under the reaction conditions used in general serve as inert solvents. These include, preferably, ethers, such as, for example, tetrahydrofuran or glycol dimethyl ether (glyme).

known-methods [Houben-Weyl, Methoden der organischen Chemie (Methods of Organic Chemistry), volume VIII and volume E5, Georg Thieme Verlag, Stuttgart 1952 and 1985].

Aliphatic carboxylic acid bromides, carboxylic acid chlorides or aliphatic carboxylic acid anhydrides are preferred here. Acetyl bromide, acetyl chloride, acetic anhydride and trifluoroacetic anhydride are particularly preferred.

Bases which can be employed are all the customary basic compounds which are suitable for a basic reaction procedure. These include, for example, alkali metal or alkaline earth metal hydroxides, carbonates or alcoholates, and preferably tertiary amines, triethylamine being particularly preferably used.

Inert solvents are employed are in general organic solvents which do not change under the reaction conditions used, such as, for example, hydrocarbons—such as benzene, toluene, xylene or petroleum fractions—or halogenhydrocarbons—such as e.g. methylene chloride, chloroform or carbon tetrachloride, or, preferably, ethers—such as diethyl ether, glycol dimethyl ether (glyme), diglycol dimethyl ether (diglyme) and particularly preferably tetrahydrofuran.

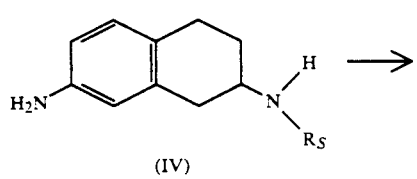

$R_A$ = H, Alkyl

III

The particular protected R- or S-diamino-1,2,3,4-tetrahydronaphthalene derivative, preferably the R- or S-7-amino-2-tert.-butoxycarbonylamido-1,2,3,4-tetrahydronaphthalene, of the general formula IV can be converted, with the processes which are known from the prior art and are particularly suitable for the preparation of acylanilides, into the correspondingly protected 7-acylamido-2amido-1,2,3,4-tetrahydronaphthalene derivatives or 7-acylamido-2-tert.-butyoxycarbonylamido-1,2,3,4-tetrahydronaphthalenes which fall within the general formula V [C. Ferri, Reaktionen der organischen Synthese (Reactions of Organic Synthesis), Georg Thieme Verlag, Stuttgart.

The reaction of the particular protected 2,7diamino-1,2,3,4-tetrahydronaphthalene derivatives or of the preferred 7amino-2-tert.-butoxycarbonyl-amido-1,2,3,4-tetrahydronaphthalene with a reactive carboxylic acid derivative in an inert solvent and in the presence of a base is preferred here. Reactive carboxylic acid derivatives are in general to be understood as carboxylic acid halides and carboxylic acid anhydrides, which can optionally be substituted by halogen atoms. Such carboxylic acid derivatives are known or can be prepared by

IV

Subsequent splitting off of the protective group $R_S$ from the amino function in the 2-position in the tetrahydronaphthalenes of the general formula V can be carried out—depending on the nature of the protective group and depending on the chemical stability of the acylanilide part structure—using the processes known from the prior art [T. W. Greene, Protective Groups in Organic Synthesis, John Wiley and Sons, New York 1981, p. 218 et seq.; U. Petersen in Houben-Weyl, Methoden der organischen Chemie (Methods of Organic Chemistry), volume E4, Georg Thieme Verlag, Stuttgart 1983, p. 144], from which the acylated 1,2,3,4-tetrahydronaphthalene derivative of the general formula VI results.

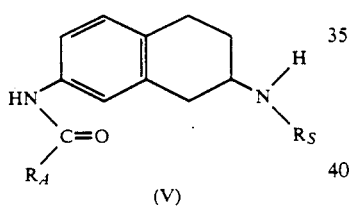

-continued

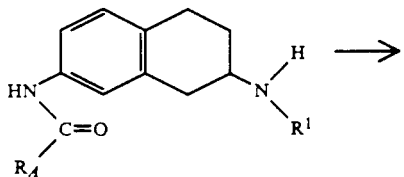

(VII)

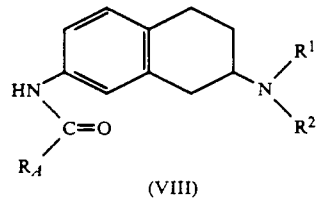

(VIII)

V

For conversion of the primary function in the 7-acylamino-2-amino-1,2,3,4-tetrahydronaphthalene derivative of the general formula VI into a secondary amine—from which a derivative of the general formula VII results—or into a tertiary amine—from which a tetrahydronaphthalene derivative of the general formula VIII results—numerous processes are likewise known from the prior art [G. Spielberger in Houben-Weyl, Methoden der organischen Chemie (Methods of Organic Chemistry), volume XI/1, Georg Thieme Verlag, Stuttgart 1957, p. 24; J. March, Advanced Organic Chemistry, 3rd ed., John Wiley and Sons, New York 1985, p. 1153].

Preferably, on the one hand, the alkylation is carried out with optionally derivatized alkyl or aralkyl halides or sulphates, tosylates or trifluoromethanesulphonates—such as e.g. methyl, ethyl, propyl, isopropyl, butyl, tert.-butyl, allyl, propargyl, benzyl, phenethyl, o-, m-and p-methylbenzyl, o-, m- and p-methoxybenzyl and omega-bromostyryl halides,
1-halogeno-2-(2-thienyl)-ethanes,
1-halogeno-2-(3-thienyl)-ethanes, benzyl halides,
allyl halides,
1-halogeno-2-phenylethanes,
1-halogeno-3-phenylpropanes,
1-halogeno-3-phenyl-prop-2enes,
1-halogeno-4-phenylbutanes,
halogenomethylcyclopropanes,
1-halogeno-3-(p-chlorophenyl)-propanes,
(2-halogenoethyl) methyl ethers,
(2-halogenoethyl) phenyl ethers (omega-halogenophenetols),
1-halogeno-3-methoxypropanes,
(2-halogenoethyl)-methyl sulphides,
(2-halogenoethyl)-phenyl sulphides,
(3-halogenopropyl)-methyl sulphides,
methyl β-halogenopropionates,
phenyl β-halogenopropionates,
β-halogenopropionic acid esters,
β-halogenopropionamides,
4-halogenobutan-2-ones,
2-(2-halogenoethyl)-furans,
3-(2-halogenoethyl)-furans,
2-(2-halogenoethyl)-pyridines,
3-(2-halogenoethyl)-pyridines,
p-(2-halogenoethyl)-methoxybenzenes,
p-(2-halogenoethyl)-toluenes,
p-(2-halogenoethyl)-methoxybenzenes,
(2-halogenoethyl)-3,4-dimethoxybenzenes,
(2-halogenoethyl)-3-chlorobenzenes,
(2-halogenoethyl)-2,4-dichlorobenzenes,
(2-halogenoethyl)-3,5-dichlorobenzenes,
1-(2-halogenoethyl)-naphthalenes,
2-(2-halogenoethyl)-naphthalenes,
(2-halogeno-1-methylethyl)-benzenes,
(2-halogenoethyl)-cyclohexanes and
2-(3-halogenoprop-2-en-1-yl)pyridines,
halogen or halide denoting chlorine, bromine or iodine, and secondly fluorine. However, for example, a sulphate half-ester, a methanesulphonic acid ester, a trifluromethylsulphonic ester or a tosylate group can be present instead of halogen or halide.

Such halides, sulphates, trifluoromethylsulphonates or tosylates are known or can be prepared by known methods, and when polyfunctional substituents which contain e.g. free phenolic hydroxyl or (carboxylic) acid functions are incorporated, their correspondingly protected derivatives—such as e.g. ethers or esters or amides—are first introduced and are converted in a further step in a conventional manner—e.g. by ether or ester cleavage—or by hydrolysis into the desired derivatives. Such derivatives include, for example, 1-brom-2-(4-methoxybenzene)ethane, ethyl bromoacetate and 3-bromopropionic acid diethylamide. Suitable solvents are all the inert organic solvents which do not change under the reaction conditions or cannot themselves intervene adversely in the course of the reaction as reactive components. These include, preferably, alcohols—such as methanol, ethanol, propanol or isopropanol—or esters—such as methyl acetate and ethyl acetate, halogenohydrocarbons, if they do not themselves act as an alkylating agent—preferably fluorohydrocarbons, and particularly preferably ethers, such as diethyl ether, di-n-butyl ether, tert.-butyl methyl ether, glycol dimethyl ether (glyme), diethylene glycol dimethyl ether (diglyme), tetrahydrofuran, dioxane and acid amides, such as, for example, hexamethylphosphoric acid triamine or dimethylformamide.

It is also possible to use mixtures of the solvents mentioned.

The reaction is preferably carried out in the presence of acid-binding agents—such as e.g. alkali metal or alkaline earth metal carbonates or bicarbonates.

VI

On the other hand, the primary amino function of the diamine of the general formula VII can be converted into the corresponding secondary or tertiary amine by the route of reductive amination of a suitable aldehyde or ketone or suitable derivatives thereof—depending on the molar ratio of the carbonyl compound employed to the 7-aceylamino-2-amino-1,2,3,4-tetrahydronaphthalene derivative of the general formula VI.

The aldehydes and ketones employed as educts are known or can be prepared by known methods [aldehydes: Houben-Weyl, Methoden der organischen Chemie (Methods of Organic Chemistry), volume VII/1and E5, Georg Thieme Verlag, Stuttgart 1954 and 1983; ketones: Houben-Weyl, Methoden der organischen Chemie (Methods of Organic Chemistry), volume VII/2a and 2b, Georg Thieme Verlag, Stuttgart 1973 and 1976].

Suitable aldehydes and ketones are embodied e.g. by formaldehyde, acetaldehyde, propionaldehyde, acetone, butyraldehyde, acrolein, propargylaldehyde, benzaldehyde, 1-naphthaldehyde, 2-naphthaldehyde, phenylacetaldehyde, 2-phenylpropionaldehyde, 3-phenylpropionaldehyde, 3-phenylacrolein (cinnamaldehyde), 4-phenylbutyraldehyde, cyclopropylformaldehyde, cyclopentylaldehyde, cyclohexylaldehyde, methoxyacetaldehyde, methylthioacetaldehyde, benzyloxyacetaldehyde, 3-methyoxypropionaldehyde, methylthioacetaldehyde, phenylthioacetaldehyde, 3-methylthiopropionaldehyde, methylthioacetaldehyde, phenylthioacetaldehyde, 3-methylthioacetaldehyde, 3-phenylthioacetaldehyde, (4-chloro)acetaldehyde, (3,4-dichlorophenyl)-acetaldehyde, 4-methoxyacetaldehyde, (3,4-dimethoxyphenyl)acetaldehyde, (3,5-dimethoxyphenyl)-acetaldehyde, (2-furyl)acetaldehyde, (3-furyl)-acetaldehyde, (2-pyridyl)-acetaldehyde, (3-pyridyl)-acetaldehyde, (4-pyridyl)-acetaldehyde, (1-naphthyl)-acetaldehyde, (2-naphthyl)-acetaldehyde and 3-(2-pyridyl)-acrolein.

The preparation is carried out in inert organic solvents, if appropriate in the presence of a catalyst and if necessary in the presence of a water-binding agent.

Suitable inert solvents here are inert organic solvents which do not change under the given reaction conditions and do not themselves intervene adversely in the course of the reaction. These include, preferably, alcohols—such as, for example, methanol, ethanol, propanol or isopropanol—or ethers, such as, for example, diethyl ether, tert.-butyl methyl ether, di-n-butyl ether, glycol dimethyl ether (glyme), diethylene glycol dimethyl ether (diglyme) or tetrahydrofuran—or halogenohydrocarbons—such as, for example, methylene chloride, chloroform or carbon tetrachloride—or carboxylic acid esters—such as, for example, methyl acetate and ethyl acetate—or hydrocarbons—such as, for example, petroleum fractions, benzene, toluene and xylene—and particularly preferably amides—such as, for example, dimethylformamide, acetamide, hexamethylphosphoric acid triamide—or carboxylic acids—such as, for example, formic acid or acetic acid—or also mixtures of the solvents mentioned.

Catalysts which are used are, if appropriate, proton acids. These include, preferably, mineral acids, such as, for example, hydrochloric acid or sulphuric acid, or organic carboxylic acids with 1 to 6 C atoms, which can optionally by substituted by fluorine, chlorine and/or bromine. Examples of such acids are formic acid, acetic acid, trifluroacetic acid, trichloroacetic acid or propionic acid. The group of preferred acids likewise includes sulphonic acids with $C_1$-$C_4$-alkyl radicals or aryl radicals, which can be optionally substituted by halogen atoms—such as, for example, methanesulphonic acid, trifluoromethanesulphonic acid, ethanesulphonic acid, benzenesulphonic acid or toluenesulphonic acid.

If necessary, the water formed during the reaction can be removed by addition of water-binding agents—such as, for example, phosphorus pentoxide—or preferably by a molecular sieve or as a mixture with the solvents employed, during or after the end of the reaction, for example by the route of distillation of the reaction mixture.

The reaction is in general carried out in a temperature range from +20° C. up to the boiling point of the particular reaction mixture, and preferably in a temperature range from +20° C. to 100° C.

The boiling point of the particular azeotrope is preferred for azeotropic distillation of the water formed during the reaction with the particular solvent or solvent mixture used.

The reaction is in general carried out under normal pressure, but can also be carried out under increased or reduced pressure.

To prepare the secondary amine, the 7-acetamido-2-amino-1,2,3,4-tetrahydronaphthalene and the particular carbonyl compound are employed in equimolar amounts. To prepare the tertiary amine, the particular carbonyl compound is employed in excess. Moreover, in the preparation of tertiary amines which fall, for example, within the general formula VIII in two-dimethylformamide as the reaction medium in the second reductive alkylation.

To achieve higher yields, it proves to be advantageous, if appropriate, in the preparation of the tetrahydronaphthalenes of the general formula VII for the amine of the general formula VI first to be subjected to reductive amination with benzaldehyde.

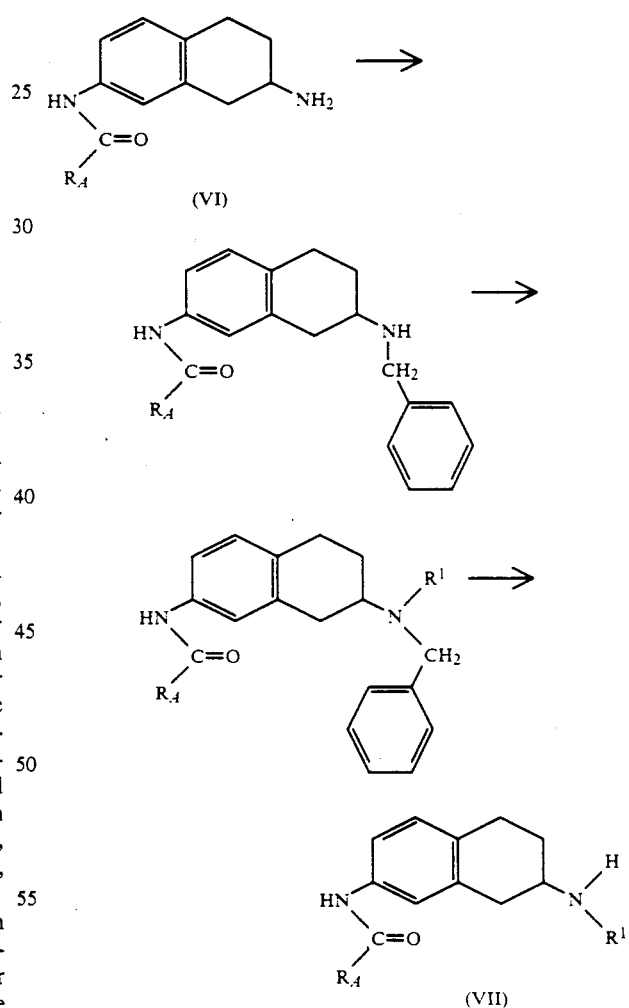

After introduction of the desired substituent, the benzyl protective group is split off. Reductive amination with benzaldehyde and splitting off of the benzyl protective group from the tertiary amine resulting after further alkylation are known from the prior art [T. W. Greene, Protective Groups in Organic Synthesis, John Wiley and Sons, New York 1981, p. 272 et seq. and [it. cit.].

The Schiff's bases or enamines or immonium salts obtained as intermediate products in the preparation of secondary or tertiary amines can be hydrogenated or reduced either by hydrogen in water or in inert organic solvents, such as alcohols, ethers or halogenohydrocarbons, or mixtures thereof with water, in the presence of suitable catalysts, or with complex hydrides—if appropriate in the presence of a catalyst. The reduction here can be carried out in the same reaction medium or in a different solvent or in a different solvent mixture. In the latter case, the solvent or solvent mixture initially employed is preferably removed by distillation.

Catalysts which are used in the catalytic reduction with hydrogen are, for example, Raney nickel, palladium, palladium-on-animal charcoal, platinum and, preferably, palladium-on-charcoal (10% Pd content).

Complex hydrides or boron or of aluminum are preferably employed in the reduction with hydrides. Lithium aluminum hydride and sodium borohydride are particularly preferably used.

Suitable solvents are all the inert organic solvents which remain unchanged or at least largely unchanged under the chosen reaction conditions and do not intervene adversely in the course of the reaction. These include amides—such as, for example, dimethylformamide or hexamethylphosphoric acid triamide—or esters—such as methyl acetate or ethyl acetate—or ethers—such as, for example, diethyl ether, tert.-butyl methyl ether, di-n-butyl ether, glycol dimethyl ether (glyme), diglycol dimethyl ether (diglyme), tetrahydrofuran and dioxane—and particularly preferably alcohols—for example methanol, ethanol, propanol or isopropanol.

Catalysts used are, if appropriate, proton acids. These include, preferably, mineral acids, such as, for example, hydrochloric acid or sulphuric acid, or organic acids with 1 to 6 C atoms, which can optionally be substituted by fluorine, chlorine and/or bromine. Examples of such acids are formic acid, acetic acid, trifluoroacetic acid, trichloroacetic acid or propionic acid. The preferred acids likewise includes sulphonic acids with $C_1$-$C_4$-alkyl radicals or aryl radicals, which can optionally be substituted by halogen atoms, such as, for example, methanesulphonic acid, trifluoromethanesulphonic acid, ethanesulphonic acid, benzenesulphonic acid or toluenesulphonic acid.

In the reduction with hydrogen, the reaction is carried out under the reaction conditions known for catalytic hydrogenation, depending on the particular catalysts, solvents and reactants employed [K. Harade in Patai, "The Chemistry of the Carbon-Nitrogen Double-Bond", Interscience Publishers, London 1970, p. 276 and lit. cit.; P. No. Rylander, Catalytic Hydrogenation over Platinum Metals, Academic Press, New York 1967, p. 123; F. Müller and R. Schröter in Houben-Weyl, Methoden der organischen Chemie (Methods of Organic Chemistry), volume XI/1, Georg Thieme Verlag, Stuttgart 1957, p. 602; W. S. Emerson, Org. Reactions 4 (1949) 174; E. M. Hancock and A. C. Cope, Org. Synth., coll. vol. III (1955) 501; J. C. Robinson and H. R. Snyder, Org. Synth., coll. vol. III (1955) 717; D. M. Malcolm and C. R. Noller, Org. Synth., coll. vol. IV (1963) 603].

The hydrogenation is preferably carried out with palladium-on-charcoal (10% Pd content) in methanol in a temperature range from 20° to 50° C.—particularly preferably in a temperature range from 25° C. to 35° C.—under a hydrogen pressure of preferably 0.1 to 0.8 MPa—particularly preferably under a hydrogen pressure of 0.4 to 0.6 MPa.

In carrying out the process according to the invention using complex hydrides, it has proved advantageous to react the amine with the corresponding aldehyde or ketone in a one-pot reaction using an inert solvent, preferably a carboxylic acid amide, and particularly preferably using dimethylformamide, in a temperature range between 50° C. and 100° C. to distill off the solvent under reduced pressure when the reaction has ended, to dissolve or disperse the residue which remains in an organic solvent—preferably an alcohol—and to react it with at least an equimolar amount of a reducing agent—preferably a complex hydride, and particularly preferably sodium borohydride—to work up the mixture by hydrolysis when the reduction has ended and to isolate the reaction product from the reaction mixture by extraction and if appropriate purify it by chromatography or subject it to a purification step by a different route and to isolate it.

VII

The preparation of the compounds according to the invention in the context of reductive amination can be carried out in another synthesis variant by the route of a Leukart-Wallach reaction, which is particularly suitable for the preparation of tertiary amides. The reaction conditions for such reductive aminations are known [collected authors, Organikum, VEB Deutscher Verlag der Wissenschaften, Berlin 1986 (16th edition) P. 491; C. Ferri, Reaktionen der organischen Synthese (Reactions of Organic Synthesis), Georg Thieme Verlag, Stuttgart 1978, p. 133 and lit. cit.; F. Möller and R. Schröter in Houben-Weyl, Methoden der oreganischen Chemie (Methods of Organic Chemistry), volume XI/1, Georg Thieme Verlag, Stuttgart 1957, p. 648].

The compounds according to the invention can moreover be prepared by any other reaction-starting from primary amines as the amine component—for example by the route of a Mannich reaction [C. Ferri, Reaktionen der organischen Synthese (Reactions of Organic Synthesis), Georg Thieme Verlag, Stuttgart 1978. p. 302 et. seq. and 496 et. seq.].

The tertiary amines of the general formula VIII according to the invention can likewise be obtained by combination of the preparation methods mentioned.

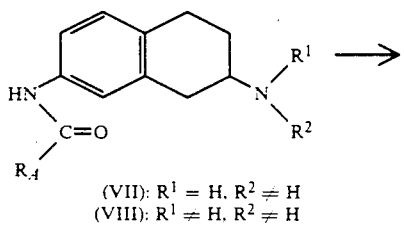

(VII): $R^1 = H, R^2 \neq H$
(VIII): $R^1 \neq H, R^2 \neq H$

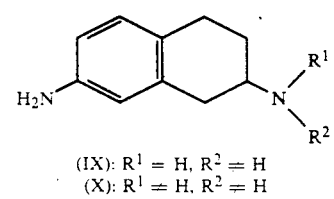

(IX): $R^1 = H, R^2 = H$
(X): $R^1 \neq H, R^2 = H$

VIII

The acyl group can be split off for further derivation of the anilinic amino function, from which the diamines of the general formulae IX and X result.

The hydrolysis of such acrylamides is known and can be achieved by reaction of a carboxylic acid amide of the general formula VII or VIII, for example by reaction of the acid amides with aqueous solutions of alkali metal hydroxides or acids [F. Möller in Houben-Weyl, Methoden der organischen Chemie (Methods of Organic Chemistry), volume XI/1, Georg Thieme Verlag Stuttgart 1957, p. 927 et. seq. and 934 et seq.; R. M. Herbst and D. Shemin, Org. Synth., coll. vol. II (1943) 491; P. E. Fanta and D. S. Tarbell, Org. Synth., coll. vol. III (1955) 661]. The reaction with dilute mineral acids under reflux conditions is preferred, hydrolysis with 2 N hydrochloric acid being particularly preferred, this immediately giving, in a one-pot reaction, the corresponding hydrochlorides, which can be isolated after removal of the reaction medium and of the volatile constituents of the reaction mixture by distillation—preferably under reduced pressure—and suspending in an organic solvent—preferably an alcohol, ether being particularly preferred—and after filtration and drying.

IX

If alkylation of the free anilinic nitrogen resulting from the splitting off is desired, this can be carried out—depending on whether a secondary or tertiary amine is required—with the methods described under V and/or VI and/or VII, from which di-, tri- or tetrasubstituted 2,7-diamino-1,2,3,4-tetrahydronaphthalene derivatives of the general formula XII, XIII, XIV or XV result.

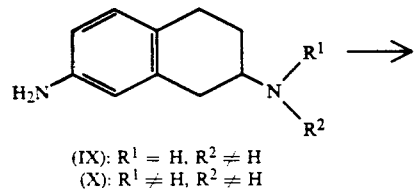

(IX): $R^1 = H$, $R^2 \neq H$
(X): $R^1 \neq H$, $R^2 \neq H$

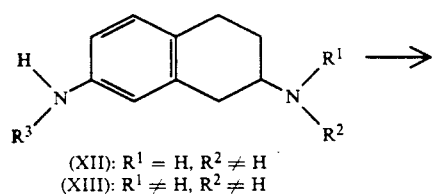

(XII): $R^1 = H$, $R^2 \neq H$
(XIII): $R^1 \neq H$, $R^2 \neq H$

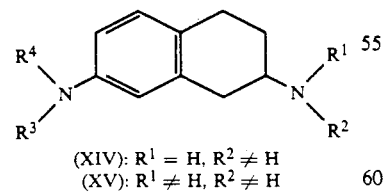

(XIV): $R^1 = H$, $R^2 \neq H$
(XV): $R^1 \neq H$, $R^2 \neq H$

X

Formylation or renewed acylation of the 2,7-diamino-1,2,3,4-tetrahydronaphthalene derivatives of the general formula X can be carried out e.g. with the methods described under III or by aminolysis, which is likewise well-known from the prior art, of the correspondingly desired carboxylic acid esters [J. March, Advanced Organic Chemistry, 3rd Ed., John Wiley and Sons, New York 1985, p. 375 and lit. cit.].

XI

Moreover, reaction of the 2,7-diamino-1,2,3,4-tetrahydronaphthalenes of the general formula X with alkali metal cyanates—preferably potassium cyanate—preferably in aqueous reaction media renders urea derivatives of the general formula XVI available.

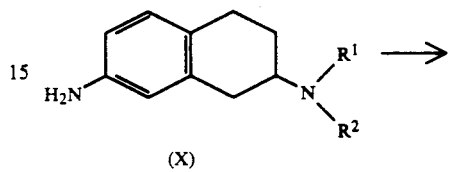

(X)

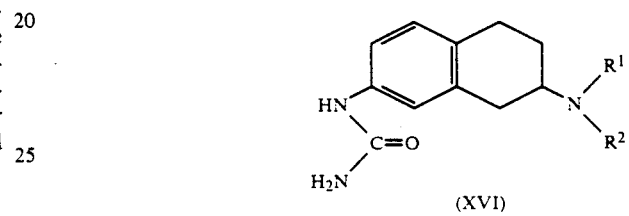

(XVI)

The processes required for this are likewise well-known from the prior art [C. Ferri, Reaktrionen der organischen Synthese (Reactions of Organic Synthesis), Georg Thieme Verlag, Stuttgart 1978, p. 657 and lit. cit.].

XII

Starting from the 7-acylamido-2-amino-1,2,3,4-tetrahydronaphthalenes of the general formula VIII, in a further synthesis variant—retaining the original acyl group—if desired further alkylation can be carried out on the amido nitrogen, from which 1,2,3,4-tetrahydronaphthalene derivatives of the general formula XVII result:

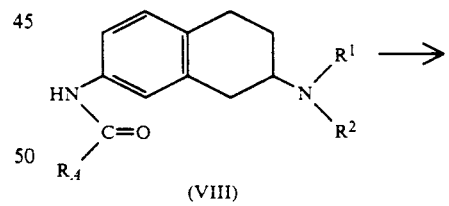

(VIII)

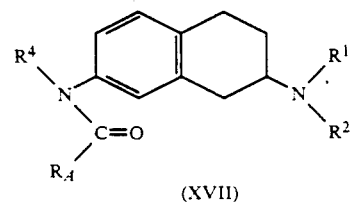

(XVII)

For the purpose of substitution on the amido nitrogen, in general the alkali metal derivatives—preferably the sodium derivatives—of the corresponding acid amides are reacted here with the desired alkyl or aralkyl halide [G. Spielberger in Houben-Weyl, Methoden der organischen Chemie (Methods of Organic Chemistry), Georg Thieme Velag, Stuttgart 1957, p. 96; W. F.

Fones, J. Org. Chem. 14 (1949) 1099; R. A. W. Johnstone, D. W. Payling and C. Thomas, J. Chem. Soc. [C] 1969, 2223].

Suitable reaction media for this are ethers—such as glycol dimethyl ether (glyme), diglycol dimethyl ether (diglyme) or tetrahydrofuran—or sulphoxides—such as dimethylsulphoxide—or acid amides, amongst which dimethylformamide is particularly preferred.

The reaction—preferably with sodium hydride as the base—is preferably carried out in a temperature range from −10° C. to 40° C., and particularly preferably in a temperature range from 0° C. to 10° C., depending on the solvent used, whereas the reaction of the resulting sodium acylamide is carried out in a temperature range from 0° C. up to the boiling point of the reaction mixture, depending on the reactivity of the halogeno-organyl employed, and if dimethylformamide is used as the reaction medium, preferably at the reflux temperature of the reaction mixture.

XIII

In another synthesis variant, the acid amide function is reduced to the corresponding secondary or tertiary amine, from which diamines of the general formula XVIII result:

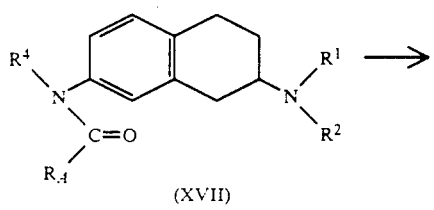

(XVII)

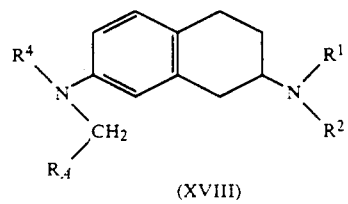

(XVIII)

Such reductions of acid amides are known from the prior art and can be effected by the route of electrolytic reduction, by reduction with alkali metals and by catalytic reduction [R. Schröter in Houben-Weyl, Methoden der organischen Chemie (Methods of Organic Chemistry), volume XI/1, Georg Thieme Verlag, Stuttgart 1957, p. 574] or with diborane or boron hydride derivatives [J. Fuhrhop and G. Penzlin, Organic Synthesis—Concepts—Methods—Starting Materials, VCH-Verlagsgesellschaft, Weinheim 1986, p. 90].

The reduction is preferably carried out with complex hydrides, such as alkali metal boro- or alkali metal aluminum hydrides, or with suitable derivatives thereof—if appropriate in the presence of a catalyst—[N. G. Gaylord, Reduction with Complex Metal Hydrides, Wiley New York 1965; A. Hajos, Complex Hydrides, Elsevier New York 1979; V. Bazant, M. Capka, M. Cerny, V. Chvalovsky, K. Kochloefl, M. Kraus and J. Malek, Tetrahedron Lett. 9 (1968) 3303], lithium aluminum hydride being particularly preferred.

Suitable reaction media here are all the inert organic solvents which do not change under the given reaction conditions. These include, preferably, ethers, such as e.g. tert.-butyl methyl ether, di-n-butyl ether, glycol dimethyl ether (glyme), diglycol dimethyl ether (diglyme), tetrahydrofuran, dioxane and particularly preferably diethyl ether.

All the general formulae II to XVIII fall under the claim of the general formula I.

The active compounds according to the invention are administered in individual doses of 1 to 300 mg, preferably 10 to 150 mg (orally) or 1 to 20 mg (parenterally).

The active compounds according to the invention can be brought into the customary galenical use forms, such as tablets, coated tablets, solutions, emulsions, powders, capsules or depot forms, it being possible to use the customary pharmaceutical auxiliaries and the customary manufacturing methods for their production. Corresponding tablets can be obtained, for example, by mixing the active compounds with known auxiliaries, for example inert diluents, such as calcium carbonate, calcium phosphate or lactose, disintegrating agents, such as maize starch or alginic acid, binders, such as starch or gelatin, lubricants, such as magnesium stearate or talc, and/or agents to achieve a depot effect, such as carboxymethylcelluslose, cellulose acetophthalate or polyvinyl acetate.

The tablets can also consists of several layers. Coated tablets can correspondingly be produced by coating cores, prepared analogously to the tablets, with the agents usually employed in coated tablet coatings, for example Kollidon or Shellac, gum arabic, talc, titanium dioxide or sugar. The core can also consists of several layers in order to achieve a depot effect or to avoid incompatibilities. The coated tablet shell can similarly consist of several layers in order to achieve a depot effect, it being possible for the auxiliaries mentioned above for the tablets to be used.

Elixirs of the active compounds or active compound combinations according to the invention can additionally also contain a sweetening agent, such as saccharin, cyclamate, glycerol or sugar, and a flavour-improving agent, e.g. aroma substances, such as vanillin or orange extract. They can moreover contain suspending auxiliaries or thickeners, such as sodium carboxymethyl-cellulose, wetting agents, for example condensation products of fatty alcohols with ethylene oxide, or preservatives, such as p-hydroxybenzoates.

Injection solutions are prepared in the customary manner, e.g. with the addition of preservatives, such as p-hydroxybenzoates, or stabilizers, such as Komplexons, and bottled in injection bottles or ampules.

The capsules containing active compounds or active compound combinations can be produced, for example, by mixing the active compounds with inert carriers, such as lactose or sorbitol, and encapsulating the mixture in gelatin capsules.

Suitable suppositories can be produced, for example, by mixing the active compounds or active compound combinations intended for these with the customary carriers, such as neutral fats or polyethylene glycol or derivative thereof.

FORMULATION EXAMPLES

| 1. Tablets | |
|---|---|
| Compound according to example 11 | 10.0 mg |
| Maize starch | 99.0 mg |
| Sec. calcium phosphate | 140.0 mg |
| Magnesium stearate | 1.0 mg |
| | 250.0 mg |

The constituents are processed in the customary manner to tablets weighing 250 mg.

| 2. Capsules | |
|---|---|
| Compound according to example 11 | 150.0 mg |
| Maize starch | 150.0 mg |
| | 300.0 mg |

The finely powders components are mixed intensively. The customary gelatin capsules are filled with 300 mg portions of the mixture.

The following preparation examples illustrate the invention without limiting it.

The prefix (+)/(−) given before the substance designations in the preparation examples is intended to mean that these syntheses can be carried out both with the laevorotatory and with the dextrorotatory optical isomers or with a mixture thereof or the corresponding racemate. All the yield data relate to % of theory.

EXAMPLE 1

Resolution of enantiomeric 2,7-diamino-1,2,3,4-etrahydronaphthalenes 81.0 g (0.5 mol) 2,7-diamino-1,2,3,4-tetrahydronaphthalene are dissolved in 1 l of a methanol/water mixture (95:5) and the solution is heated to 50° C. A solution of 37.5 g (0.25 mol) L-(+)-tartaric acid in 200 ml methanol is added at this temperature. The crystals which have precipitated after a short time are filtered off with suction, boiled up three times with 300 ml methanol/water mixture (95:5) each time and recrystallized once from water. The tartrate is then suspended in 70 ml water, 33 g (0.6 mol) potassium hydroxide are added and the mixture is extracted twice with 70 ml tetrahydrofuran each time. After the organic phase has been dried with magnesium sulphate and the desiccant has been filtered off, the solvent is removed i. vac. and the residue is distilled under a reduced pressure of 0.08 hPa.

(+)-2,7-Diamino-1,2,3,4-tetrahydronaphthalene is isolated as colourless crystals.

Yield: 9.7 g (12%)
m.p.: 33°–34° C.
b.p.: 108°–110° C.

The (−)-enantiomer is obtained by an analogous route using R-(−)-tartaric acid.

Yield: 9.8 g (12%)
m.p.: 33°–34° C.
b.p.: 108°–110° C.

In the following examples, in each case (+)-2,6-diamino-1,2,3,4-tetrahydronaphthalene or (−)-2,7-diamino-1,2,3,4-tetrahydronaphthalene is used as the starting substance to prepare the enantiomerically pure compounds.

EXAMPLE 2

(+)/(−)-7-Amino-2-tert.-butoxycarbonylamido-1,2,3,4-tetrahydronaphthalene

A solution of 28.7 ml (0.12 mol) di-tert.-butyl pyrocarbonate in 140 ml anhydrous tetrahydrofuran is added dropwise to a solution of 20 g (0.12 mol) (+)/(−)-2,7-diamino-1,2,3,4-tetranaphthalene and 17.1 ml (0.12 mol) triethylamine in 250 ml anhydrous tetrahydrofuran at −10° C. The reaction mixture is subsequently stirred at −10° C. for 30 minutes and then allowed to warm to room temperature. The solvent is distilled off i. vac., 500 ml ethyl acetate are added to the residue and the mixture is washed twice with 100 ml water each time.

The organic phase is then dried with magnesium sulphate, the solvent is removed i. vac. and the residue is recrystallized from diethyl ether.

Yield: 25 g (80%)
m.p.: 119°–121° C.

EXAMPLE 3

(+)/(−)-7-Acetamido-2-tert.-butoxycarbonylamido-1,2,3,4-tetrahydronaphthalene 25 g (95 mmol) 7-amino-2-tert.-butoxycarbonylamido-1,2,3,4-tetrahydronaphthalene and 14.5 ml (100 mmol) triethylamine are dissolved in 120 ml anhydrous tetrahydrofuran, and 9.9 ml (105 mmol) acetic anhydride are added at room temperature. The mixture is subsequently stirred at room temperature for 1 hour and 450 ml ice-water are then added. The crystals which have precipitated are filtered off with suction, washed with 200 ml water, with 35 ml acetone and with 60 ml diethyl ether and dried to constant weight in a circulating air drying cabinet.

Yield: 25.9 g (93%)
m.p.: 193°–195° C.

EXAMPLE 4

(+)/(−)-7-Acetamido-2-amino-1,2,3,4-tetrahydronaphthalene hydrochloride 50 g (0.16 mol) 7-acetamido-2-tert.-butoxycarbonylamido-1,2,3,4tetrahydronaphthalene are suspended in 300 ml ethanol. A vigorous stream of HCl gas is passed through the suspension for about 10 minutes, the temperature being allowed to rise to 70° C. The mixture is allowed to cool to room temperature and the crystals which have precipitated are filtered off with suction, washed once each with 100 ml acetone and 100 ml diethyl ether and dried in a circulating air cabinet, first at room temperature and then to constant weight at 80° C. under normal pressure.

Yield: 36 g (91%)
m.p.: 260° C.

EXAMPLE 5

(+)/(−)-7-Acetamido-2-propylamino-1,2,3,4-tetrahydronaphthalene hydrochloride (alkylation)

83.8 g (0.41 mol) (+)/(−)-7-acetamido-2-amino-1,2,3,4-tetrahydronaphthalene and 75.6 g (0.61 mol) propyl bromide are dissolved in 900 ml tetrahydrofuran, 84 g (0.84 mol) potassium bicarbonate are added and the mixture is heated at the reflux temperature for 7 hours. A further 75.6 g (0.61 mol) propyl bromide are then added and the mixture is heated at the boiling point again for 7 hours. It is allowed to cool to room temperature and filtered, the filtrate is concentrated i. vac., 500 ml acetic acid are added and the mixture is extracted with 500 ml water. The organic phase is dried with magnesium sulphate and, after filtering off the desiccant, the filtrate is concentrated i. vac. and the residue which remains is chromatographed on silica gel (particle size 0.063 to 0.2 mm) with a mixture of methylene chloride and methanol (80:20).

After isolation by chromatography, concentration of the eluate: i. vac. and reaction of the residue with a solution of hydrogen chloride in diethyl ether, the title compound is precipitated as the hydrochloride, filtered off the dried to constant weight in a circulating air drying cabinet.

Yield: 43.4 g (38%)

m.p.: 171° C.

The hydrochlorides of the following compounds are prepared analogously to example 5, dimethylformamide being employed as the reaction medium for preparation of the dialkylated 7-acetamido-2-dialkyl- and 7-acetamido-2-alkylaralkyl-1,2,3,4-tetrahydronaphthalene derivatives:

TABLE 5

| $R^1$ | $R^2$ | $R^3$ | $R^4$ | m.p.: |
|---|---|---|---|---|
| H | $C_2H_5$ | Acetyl | H | 212–214° C. |
| H | $CH_2-CH_2$-(thiophen-2-yl) | Acetyl | H | 233–234° C. |
| H | $CH_2-CH_2$-(thiophen-3-yl) | Acetyl | H | 231–233° C. |
| Butyl | $(CH_2)_3-CH_3$ | Acetyl | H | 178–180° C. |
| Propyl | $(CH_2)_3-CH_3$ | Acetyl | H | 226–228° C. |
| Propyl | $CH_2-CH_2$-(thiophen-3-yl) | Acetyl | H | from 95° C. |
| Propyl | $CH_2$-phenyl | Acetyl | H | 103–106° C. |
| Propyl | $CH_2-CH_2$-phenyl | Acetyl | H | 117–120° C. |
| Propyl | $CH_2-CH_2-CH_2$-phenyl | Acetyl | H | 106–109° C. |
| Propyl | $CH_2-CH=CH_2$ | Acetyl | H | 257–258° C. |
| Propyl | $CH_2-CH=CH$-phenyl | Acetyl | H | from 135° C. |
| Allyl | $CH_2-CH=CH_2$ | Acetyl | H | 228–230° C. |
| Propyl | $CH_2-C\equiv CH$ | Acetyl | H | 231–233° C. |
| Propyl | $CH_2-CH_2$-(thiophen-2-yl) | Acetyl | H | from 105° C. |
| Propyl | $(CH_2)_4$-phenyl | Acetyl | H | from 82° C. |
| Propyl | $CH_2-CH_2$-(4-chlorophenyl) | Acetyl | H | 107–110° C.[1] |
| Propyl | $CH(CH_3)_2$ | Acetyl | H | 104–106° C.[1] |
| Propyl | $CH_2$-cyclopropyl | Acetyl | H | 105–107° C.[1] |

TABLE 5-continued

| $R^1$ | $R^2$ | $R^3$ | $R^4$ | m.p.: |
|---|---|---|---|---|
| $(CH_2)_3-$ | $(CH_2)_3-\phenyl$ | Acetyl | H | from 94° C. |
| Propyl | $CH_2-CH_2-CH_2-\phenyl-Cl$ | Acetyl | H | from 106° C. |

TABLE 6

| | $R^1 =$ Propyl, $R^3 =$ Acetyl, $R^4 =$ H | |
|---|---|---|
| $R^2$ | $[\alpha]_D^{20\,2}$ | m.p.: |
| $(CH_2)_3-CH_3$ | −79.2° | 208–210° C. |
| $(CH_2)_3-CH_3$ | +78.5° | 208–210° C. |
| $CH_2-CH_2-\phenyl$ | −54.7° | from 115° C. |
| $CH_2-CH_2-\phenyl$ | +55.3° | from 115° C. |
| $CH_2-CH_2-CH_2-\phenyl$ | −62.9° | from 92° C. |
| $CH_2-CH_2-CH_2-\phenyl$ | +63.7° | from 88° C. |
| $CH_2-CH=CH-\phenyl$ | −110.3° | from 125° C. |
| $CH_2-CH=CH-\phenyl$ | +103.4° | 84–86° C.[1] |

[1] melting point of the free base
[2] in methanol c = g.dm/100 ml

EXAMPLE 6

(+)/(−)-7-Acetamido-2-[(3-phenylallyl)amino]-1,2,3,4-tetrahydronaphthalene hydrochloride (reductive amination with sodium tetrahydridoboranate [NaBH₄])

4.8 g (23 mmol) (+)/(−)-7-acetamido-2-amino-1,2,3,4-tetrahydronaphthalene and 3 g (23 mmol) cinnamaldehyde are dissolved in 50 ml dimethylformamide and the solution is stirred at 100° C. for one hour. Thereafter, the solvent is distilled off i. vac. and 50 ml ethanol and −1 g (26 mmol) sodium tetrahydridoboranate (NaBH₄) are added to the residue. The mixture is subsequently stirred at 30°–40° C. for 1 hour and the solvent is then removed i. vac. 200 ml ethyl acetate are added to the residue and the mixture is washed twice with 100 ml water each time and extracted once with 200 ml 2 N HCl. The aqueous extract is then rendered alkaline with conc. aqueous ammonia solution and extracted twice with 100 ml ethyl acetate each time; the organic phase is dried with magnesium sulphate and, after removal of the desiccant by filtration, the filtrate is concentrated i. vac. The residue which remains is dissolved in ethanol, and ethereal hydrogen chloride solution is added to precipitate the hydrochloride. The crystals are filtered off with suction and dried to constant weight in a circulating air drying cabinet.

Yield: 5 g (60%)
m.p.: 253°–255° C.

(+) and (−)-7-acetamido-2-benzylamino-1,2,3,4-tetrahydronaphthalene are prepared analogously to example 6.

Yield: 86%
m.p.: 233°–234° C.

EXAMPLE 7

(+)/(−)-7-Acetamido-2-N,N-diethylamino-1,2,3,4-tetrahydronaphthalene hydrochloride (reductive amination with hydrogen)

6.5 g (32 mmol) 7-acetamido-2-amino-1,2,3,4-tetrahydronaphthalene and 22 g (500 mmol) acetaldehyde are dissolved in 110 ml methanol, and 2.2 g palladium/charcoal (10% Pd) are added. The mixture is hydrogenated in an autoclave at 30° C. under a hydrogen pressure of 500-kPa for 18 hours. It is then filtered with suction over silica gel and the solvent is distilled off i. vac. 150 ml diethyl ether are then added to the residue and the mixture is washed twice with 60 ml water each time. The organic phase is dried with magnesium sulphate and, after filtering off the desiccant, the solvent is removed from the filtrate i. vac. and the residue which remains is chromatographed on silica gel (particle size 0.063–0.2 mm, mobile phase: ethyl acetate/methanol; 80:20). After isolation by chromatography, the eluate is concentrated and (+)/(−)-acetamido-2-N,N-diethylamino-1,2,3,4hydrochloric acid. The crystals are filtered off with suction and dried to constant weight in a circulating air drying cabinet.

Yield: 1.7 g (18%) m.p.: >265° C.

EXAMPLE 8

(+)/(−)-7-Acetamido-2-(N-allyl-N-methyl)amino-1,2,3,4-tetrahydronaphthalene hydrochloride (Leukart-Wallach amination)

2.0 g (8.2 mmol) (+)/(−)-7-acetamido-2-allylamino-1,2,3,4-tetrahydronaphthalene are dissolved in 40 ml 99 percent formic acid, and 10 ml aqueous 30 percent formalin solution are added. The mixture is heated at the reflux temperature for 1.5 hours and concentrated i. vac., ice is added to the residue and the mixture is rendered alkaline with conc. aqueous Thereafter, the mixture is extracted twice with 100 ml ethyl acetate each time, the combined organic phases are dried with magnesium sulphate and, after removal of the desiccant by filtration, the solvent is distilled off i. vac. The residue which remains is chromotographed on silica gel (particle size 0.063-0.2 mm, mobile phase: methylene chloride/methanol; 80:20). After isolation of (+)/(−)-7-acetamino-2-(N-allyl-N-methyl)amino-1,2,3,4-tetrahydronaphthalene by chromatography, the eluate is concentrated and the base is converted into the hydrochloric with etheral hydrochloric acid. The crystals are filtered off with suction and dried to constant weight in a circulating air drying cabinet.

Yield: 1.8 (75%)
m.p.: 169°-171° C.

(+)/(−)-7-Acetamido-2-[N-methyl-N-(3-phenylallyl)amino-1,2,3,4-tetrahydronaphthalene is prepared analogously to example 8:

Yield: 35%
m.p.: 249°-251° C.

EXAMPLE 9

(+)/(−)-7-Amino-2-ethylamino-1,2,3,4-tetrahydronaphthalene hydrochloride 1.6 (5.9 mmol) (+)/(−)-7-acetamido-2-ethylamino-1,2,3,4-tetrahydronaphthalene hydrochloride are heated at the reflux temperature with 40 ml 2 N HCl for 2 hours. The solution is then concentrated i. vac., 20 ml ethanol are added to the residue and the crystals are filtered off with suction, washed with ethanol and dried to constant weight in a circulating air drying cabinet.

Yield: 1.3 g (84%)
m.p.: >260° C.

TABLE 7

The hydrochlorides of the following compounds were prepared analogously to example 9

| $R^1$ | $R^2$ | $R^3$ | $R^4$ | m.p.: |
|---|---|---|---|---|
| H | $CH_2-CH_2-CH_3$ | H | H | 198-199° C. |
| H | $CH_2$—phenyl | H | H | from 150° C.[1] |
| H | $CH_2-CH_2$—thienyl | H | H | from 258° C.[1] |
| Ethyl | $C_2H_5$ | H | H | 153-155° C. |
| Butyl | $-(CH_2)_3-CH_3$ | H | H | 154-156° C. |
| Propyl | $CH_3$ | H | H | 178-180° C. |
| Propyl | $-(CH_2)_3-CH_3$ | H | H | 152-154° C. |
| Propyl | $CH_2$—thienyl | H | H | from 180° C. |
| Propyl | $CH_2$—thienyl | H | H | from 180° C.[1] |
| Propyl | $CH_2-CH_2$—thienyl | H | H | 187-190° C.[1] |
| Propyl | $CH_2$—phenyl | H | H | 165-168° C. |
| Methyl | $CH_2$—phenyl | H | H | 210-212° C.[1] |
| Propyl | $CH_2-CH_2$—phenyl | H | H | 145-148° C. |
| Methyl | $CH_2-CH_2$—phenyl | H | H | 125-128° C. |

TABLE 7-continued

The hydrochlorides of the following compounds were prepared analogously to example 9

| $R^1$ | $R^2$ | $R^3$ | $R^4$ | m.p.: |
|---|---|---|---|---|
| Propyl | $CH_2-CH_2-CH_2-$phenyl | H | H | 105-108° C. |
| Propyl | $CH_2-CH=CH_2$ | H | H | 152-154° C. |
| Methyl | $CH_2-CH=CH_2$ | H | H | 79-82° C. |
| Allyl | $CH_2-CH=CH_2$ | H | H | 94-97° C. |
| H | $CH_3$ | H | H | >260° C.[1] |
| Propyl | $CH_2-CH_2-$(2-thienyl) | H | H | from 110° C.[1] |
| Propyl | $CH_2-CH_2-$(4-Cl-phenyl) | H | H | from 165° C.[1] |
| Propyl | $(CH_2)_4-$phenyl | H | H | from 135° C.[1] |
| Propyl | $CH_2-C\equiv CH$ | H | H | 70-72° C. |
| Propyl | $CH_2-$cyclopropyl | H | H | 91-93° C. |
| Propyl | $CH_2-CH=CH-$phenyl | H | H | 182-184° C.[1] |
| $(CH_2)_3-$phenyl | $(CH_2)_3-$phenyl | H | H | from 140° C.[1] |

[1]Dihydrochloride

TABLE 8

The dihydrochlorides of the following compounds were prepared analogously to example 9:
$R^1$ = Propyl, $R^3$ = H, $R^4$ = H

| $R^2$ | $[\alpha]_D^{20}$ | m.p.: |
|---|---|---|
| $-(CH_2)_3-CH_3$ | $-66.4°$ | from 150° C. |
| $-(CH_2)_3-CH_3$ | $+66.4°$ | from 151° C. |
| $CH_2-CH_2-$phenyl | $-31.6°$ | from 146° C. |
| $CH_2-CH_2-$phenyl | $+51.1°$ | from 142° C. |
| $CH_2-CH_2-CH_2-$phenyl | $-55.3°$ | from 158° C. |
| $CH_2-CH_2-CH_2-$phenyl | $+54.3°$ | from 157° C. |
| $CH_2-CH=CH-$phenyl | $-74.7°$ | from 180° C.[1] |
| $CH_2-CH=CH-$phenyl | $+88.3°$ | from 150° C.[2] |

[1]in methanol c = g.100 ml$^{-1}$.dm
[2]hydrochloride

EXAMPLE 10

(+)/(−)-2-Dipropylamino-7-methanesulphonamido-1,2,3,4-tetrahydronaphthalene hydrochloride 1.7 g (7.9 mmol) (+)/(−)-7-amino-2-dipropylamino-1,2,3,4-tetrahydronaphthalene and 1.1. ml (7.6 mmol) triethylamine are dissolved in 25 ml tetrahydrofuran. 0.9 g (7.6 mmol) mesyl chloride is added dropwise to this solution at 15° C. and the mixture is then subsequently stirred at room temperature for a further hour. Thereafter, the solvent is distilled off under reduced pressure, 200 ml ethyl acetate are added to the residue and the mixture is washed twice with 80 ml water each time. The organic phase is dried with magnesium sulphate and, after removal of the desiccant by filtration, the solvent is removed i. vac. The base which remains is converted into the crystalline hydrochloride with ethereal hydrochloric acid, and the product is dried to constant weight in circulating air drying cabinet.

Yield: 1.5 (60%)

m.p.: 256°–257° C.

(+)/(−)-2-(N-Phenethyl-N-propyl)amino-7-trifluoracetamido-1,2,3,4tetrahydronaphthalene is prepared analagously to example 10 using trifluoroacetic anhydride and by heating at the reflux temperature for 8 hours:

m.p.: from 108° C.

EXAMPLE 11

(+)/(−)-7-Formylamido-2-(N-phenethyl-N-propyl)amino-1,2,3,4-tetrahydronaphthalene hydrochloride 1.5 g (4.9 mmol) (+)/(−)-7-amino-2-(N-phenethyl-N-propyl)amino-1,2,3,4-tetrahydronaphthalene are dissolved in 20 ml methyl formate and the solution is heated at 120°C. in an autoclave for 16 hours. After cooling, the solvent is distilled off i. vac., 50 ml each of ethyl acetate and water are added to the residue and the aqueous phase is rendered alkaline with potassium carbonate. The two phases are separated and the aqueous phase is extracted twice more with 50 ml ethyl acetate each time. The combined organic extracts are dried with magnesium sulphate and, after the desiccant has been removed by filtration, the filtrate is concentrated in vacuo. The residue which remains is then chromatographed on aluminum oxide ($Al_2O_3$; N II–III) with a mixture of cyclohexane/ethyl acetate (1:1). The base isolated in this manner is freed from the solvent i. vac. and converted into the hydrochloric with ethereal hydrochloric acid.

Yield: 1.3 g (71%)

m.p.: from 98° C.

EXAMPLE 12

(+)/(−)-7-Carbamoylamido-2-N,N-dipropylamino-1,2,3,4-tetrahydronaphthalene 1.4 g (5.7 mmol) (+)/(−)-7-amino-2-N,N-dipropylamino-1,2,3,4tetrahydronaphthalene are dissolved in 20 ml water, 1.0 g potassium cyanate is added and the mixture is stirred at 80° C. for 15 minutes. After cooling, 10 ml conc. aqueous ammonia solution are added and the mixture is extracted twice with 50 ml ethyl acetate each time. The combined organic extracts are washed with 30 ml water and then dried with magnesium sulphate, and after the desiccant has been removed by filtration, the filtrate is concentrated i. vac. The residue is crystallized from petroleum ether and the crystals are dried to constant weight in a circulating air drying cabinet.

Yield: 1.1 g (67%)

m.p.: 139°–141° C.

EXAMPLE 13

(+)/(−)-2-N,N-Dipropylamino-7-(N-methyl-acetamido)-1,2,3,4tetrahydronaphthalene hydrochloride A solution of 5.5 g (19 mmol) (+)/(−)-7-acetamido-2-N,N-dipropylamino-1,2,3,4-tetrahydronaphthalene in 30 ml dimethylformamide is added dropwise to a suspension of 0.6 g (25 mmol) sodium hydride in 35 ml dimethylformamide, while cooling with ice. The mixture is subsequently stirred for about 30 min, until no further evolution of hydrogen is to be observed. 1.4 ml (22 mmol) methyl iodide are then added dropwise. Thereafter, the reaction mixture is heated at the reflux temperature for 4 hours. The solvent is distilled off i. vac., 100 ml each of ethyl acetate and water are added, the organic phase is separated off and the aqueous phase is extracted twice with 50 ml ethyl acetate each time. The combined organic extracts are dried with magnesium sulphate, after removal of the desiccant by filtration the solvent is distilled off i. vac. and the residue which remains is chromatographed on silica gel (particle size 0.063–0.2 mm) with an ethyl acetate/cyclohexane mixture (1:1). The fraction of (+)/(−)-2-dipropyl-amino-7-(N-methyl-acetamido-1,2,3,4-tetrahydronaphthalene isolated in this manner is concentrated i. vac. and the residue is converted into the hydrochloride with ethereal hydrochloric acid. The crystals are dried in a circulating air drying cabinet.

m.p.: 208°–211° C.

(+)/(−)-2-N,N-Dipropylamino-7-(N-methyl-formamido)-1,2,3,4-tetrahydronaphthalene is prepared analogously to example 13.

m.p.: 61°–62° C.

EXAMPLE 14

(+)/(−)-2-N,N-Dipropylamino-7-ethylamino-1,2,3,4-tetrahydronaphthalene hydrochloride 0.7 g (18 mmol) lithium aluminum hydride is initially introduced into 40 ml anhydrous ether. A solution of 5.9 g (18 mmol) 7-acetamido-2-N,N-dipropylamino-1,2,3,4-tetrahydronaphthalene in 50 ml anhydrous diethyl ether is added dropwise at about +10° C. over a period of 3 hours at the reflux temperature, while stirring. The reaction mixture is then heated and is subsequently allowed to cool to about 5° C., and 0.7 ml water, 2.1 ml 15 percent sodium hydroxide solution and a further 0.7 ml water are added in succession to the suspension. The precipitate formed is filtered off with suction and washed three times with 50 ml ether each time and the combined ethereal extracts are concentrated i. vac. The residue is chromotographed on silica gel (particle size 0.063–0.2 mm) with a mixture of cylcohexane and ethyl acetate (1:1). The fraction of (+)/(−)-2-N,N-dipropylamino-7-ethylamino-1,2,3,4-tetranaphthalene isolated in this manner is concentrated i. vac. and the base which remains is converted into the hydrochloride with ethereal hydrochloric acid. The crystals are dried to constant weight in a circulating air drying cabinet.

Yield: 2.1 g (32%)

m.p.: from 55° C.

EXAMPLE 15

(+)/(−)-7-Acetamido-2-methylamino-1,2,3,4-tetrahydronaphthalene hydrochloride (reductive debenzylation)

6.0 g (19 mmol) (+)/(−)-7-acetamido-2-(N-benzyl-N-methyl)amino-1,2,3,4-tetrahydronaphthalene are dissolved in 95 ml methanol, 0.6 g palladium-on-charcoal (10% Pd) is added and hydrogenation is carried out for 5 hours at 20° C. under a hydrogen pressure of 500 kPa. The reaction mixture is then filtered, the solvent is distilled off i. vac. and the residue is converted into the hydrochloride with ethereal hydrochloric acid, the product being recrystallized from methanol. The crystals are dried to constant weight in a circulating air drying cabinet.

Yield: 1.5 g (29%)

m.p.: >265° C.

What is claimed is:

1. A compound of the formula

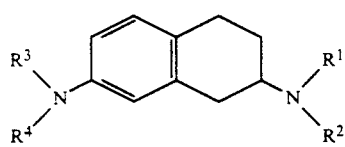

wherein $R^1$ denotes $C_1-C_{12}$ alkyl;

$R^2$ denotes $(CH_2)_b-R^7$, and b denotes the number 1, 2, 3 or 4;

$R^3$ denotes acetyl;

$R^4$ denotes hydrogen;

$R^7$ denotes

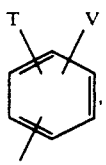

wherein

T denotes hydrogen, halogen, lower alkyl, alkoxy, OH, $NH_2$ or $NO_2$,

V denotes hydrogen, halogen, lower alkyl, alkoxy, OH $NH_2$ or $NO_2$.

2. A compound as recited in claim 1, wherein $R^1$ denotes $C_1-C_6$ alkyl;

$R^2$ denotes $(CH_2)_b-R^7$ and b denotes the number 1, 2, 3 or 4;

$R^3$ denotes acetyl;

$R^4$ denotes hydrogen.

3. A compound as recited in claim 1, wherein $R^1$ denotes $C_1-C_4$ alkyl;

$R^2$ denotes $(CH_2)_b-R^7$ and b denotes the number 1, 2, 3 or 4;

$R^3$ denotes acetyl;

$R^4$ denotes hydrogen;

$R^7$ denotes

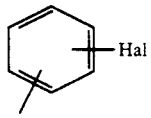

wherein HAL denotes chlorine or bromine.

4. (+) or (−)-7-Acetamido-2-(N-phenylethyl-N-propyl)amino-1,2,3,4-tetrahydronaphthalene, or acid addition salts thereof.

5. A pharmaceutical composition for treatment of schizophrenia comprising a therapeutically effective amount of a compound as recited in claims 1, 2, 3 or 4, and a pharmaceutically acceptable carrier.

6. A method for treating schizophrenia in a patient which comprises administering to the patient a therapeutically effective amount of a compound as recited in claim 1, 2, 3, or 4.

* * * * *